United States Patent
Schmedtje, Jr.

(10) Patent No.: US 11,779,560 B2
(45) Date of Patent: Oct. 10, 2023

(54) METHODS OF USING NITRIC OXIDE DONOR COMPOUNDS FOR TREATMENT OF COVID-19 AND OTHER INFECTIOUS DISEASES

(71) Applicant: COEURATIVE, INC., Roanoke, VA (US)

(72) Inventor: John Frederick Schmedtje, Jr., Roanoke, VA (US)

(73) Assignee: Coeurative, Inc., Roanoke, VA (US)

(*) Notice: Subject to any disclaimer, the term of this patent is extended or adjusted under 35 U.S.C. 154(b) by 0 days.

(21) Appl. No.: 17/211,778

(22) Filed: Mar. 24, 2021

(65) Prior Publication Data

US 2021/0346335 A1    Nov. 11, 2021

Related U.S. Application Data

(60) Provisional application No. 63/134,579, filed on Jan. 6, 2021, provisional application No. 63/119,539, filed on Nov. 30, 2020, provisional application No. 63/111,019, filed on Nov. 7, 2020, provisional application No. 63/033,194, filed on Jun. 1, 2020, provisional application No. 63/001,289, filed on Mar. 28, 2020.

(51) Int. Cl.
| | |
|---|---|
| *A61K 31/34* | (2006.01) |
| *A61K 9/00* | (2006.01) |
| *A61K 9/12* | (2006.01) |
| *A61K 9/20* | (2006.01) |
| *A61K 9/48* | (2006.01) |
| *A61K 47/02* | (2006.01) |
| *A61K 47/10* | (2017.01) |
| *A61K 47/12* | (2006.01) |
| *A61K 47/18* | (2017.01) |
| *A61K 47/20* | (2006.01) |

(52) U.S. Cl.
CPC ............ *A61K 31/34* (2013.01); *A61K 9/0014* (2013.01); *A61K 9/0019* (2013.01); *A61K 9/12* (2013.01); *A61K 9/2018* (2013.01); *A61K 9/2027* (2013.01); *A61K 9/2059* (2013.01); *A61K 9/4825* (2013.01); *A61K 9/4858* (2013.01); *A61K 9/4866* (2013.01); *A61K 47/02* (2013.01); *A61K 47/10* (2013.01); *A61K 47/12* (2013.01); *A61K 47/183* (2013.01); *A61K 47/186* (2013.01); *A61K 47/20* (2013.01)

(58) Field of Classification Search
CPC .... A61K 31/34; A61K 9/0014; A61K 9/0019; A61K 9/12; A61K 9/2018; A61K 9/2027; A61K 9/2059; A61K 9/4825; A61K 9/4858; A61K 9/4866; A61K 47/02; A61K 47/10; A61K 47/12; A61K 47/183; A61K 47/186; A61K 47/20; A61P 31/04; A61P 31/12
See application file for complete search history.

(56) References Cited

U.S. PATENT DOCUMENTS

| | | | | |
|---|---|---|---|---|
| 10,501,471 | B1* | 12/2019 | Schmedtje, Jr. | ..... C07D 493/04 |
| 10,913,748 | B2* | 2/2021 | Schmedtje, Jr. | ..... A61K 9/2018 |

OTHER PUBLICATIONS

Finbloom et al., Engineering the drug carrier biointerface to overcome biological barriers to drug delivery. Advanced Drug Delivery Reviews. 167, 2020, 89-108. (Year: 2020).*
ISR/WO dated Oct. 22, 2021 for PCT/US2021/024540.
Wang reference in ISR/WO dated Oct. 22, 2021 for PCT/US2021/024540.

* cited by examiner

*Primary Examiner* — Susanna Moore
*Assistant Examiner* — Luisalberto Gonzalez

(57) ABSTRACT

The present invention provides novel methods of using nitric oxide donor compounds for treating infectious diseases, for example, COVID-19.

19 Claims, 12 Drawing Sheets

METHODS OF USING NITRIC OXIDE DONOR COMPOUNDS FOR TREATMENT OF COVID-19 AND OTHER INFECTIOUS DISEASES

CROSS-REFERENCE TO RELATED APPLICATIONS

This application claims the benefit of U.S. Provisional Patent Application No. 63/134,579 filed Jan. 6, 2021, which is incorporated by reference herein in its entirety.

This application claims the benefit of U.S. Provisional Patent Application No. 63/119,539 filed Nov. 30, 2020, which is incorporated by reference herein in its entirety.

This application claims the benefit of U.S. Provisional Patent Application No. 63/111,019 filed Nov. 7, 2020, which is incorporated by reference herein in its entirety.

This application claims the benefit of U.S. Provisional Patent Application No. 63/033,194 filed Jun. 1, 2020, which is incorporated by reference herein in its entirety.

This application claims the benefit of U.S. Provisional Patent Application No. 63/001,289 filed Mar. 28, 2020, which is incorporated by reference herein in its entirety.

FIELD OF THE INVENTION

The present invention provides novel methods of using nitric oxide donor compounds for treating infectious diseases, for example, COVID-19.

BACKGROUND OF THE INVENTION

The SARS-CoV-2 virus and the associated COVID-19 pandemic have had a negative effect on public health worldwide. A safe and effective therapeutic regimen that could prevent outbreaks and/or reduce morbidity or mortality would have a major impact on the pandemic and mitigate the disruptive effects of COVID-19 on human society and the world economy. Vaccine development and periodic refinement will be part of the solution, but long term outcomes and vaccine safety are uncertain, while public acceptance is limited and what is described as COVID-19 herd immunity may be impossible to achieve. It seems most likely that no one method of pandemic control will be entirely satisfactory and that a combination of immunizations and treatments, as well as social distancing for high risk populations, will be required indefinitely. The present invention addresses an unmet need for treatments for infectious diseases including, most urgently, COVID-19.

There are very few specific therapeutic options of merit for COVID-19 currently. However, we know that nitric oxide acts as a pulmonary vasodilator and can be of therapeutic value in hypoxemia secondary to acute respiratory distress syndrome. Nitric oxide gas has antiviral activity against other strains of coronavirus in clinical and experimental models. Novel delivery systems that facilitate NO release in systemic and pulmonary blood vessels could reduce morbidity and mortality related to COVID-19.

COVID-19 pneumonitis creates hypoxia. Death is ultimately due to oxygen deprivation. Strategies to manage this problem should include vasodilatation in the setting of oxygen deprivation and modulation of inflammatory responses. The proprietary compounds described herein are designed to address these challenges and deliver therapeutic benefits.

The SLC14 (solute carrier 14) family of urea transporter genes regulate urea transport across cell membranes. UT-B (urea transport protein B, the product of the gene SLC14A1) facilitates transport of urea, water, and urea analogues across cell membranes and is expressed in the heart, vascular endothelium, and erythrocytes. Intracellular accumulation of urea leads to increased breakdown of arginine by nitric oxide synthase instead of arginase. (Sun, Lau et al. 2016) SLC14A1 mRNA was markedly overexpressed in human vascular endothelial cells in culture under hypoxic (1% oxygen) conditions compared with normoxia (20%) in overexpression libraries derived from human vascular endothelium. Upregulation of expression of UT-B in hypoxia should lead to transport of urea out of the endothelial cell and likely contributes to the previously documented reduction in eNOS-NO pathway activity in hypoxia. (Schmedtje, Ji et al. 1997) It is desirable to develop compounds that potentiate vasodilatory release of NO in hypoxia, thereby overcoming the reduction in NO observed in hypoxia. NO also has antiviral activity by inhibiting viral proteases (Saura, Zaragoza et al. 1999) and there is inhibition of SARS-CoV infection in vitro by an NO donor. (Keyaerts, Vijgen et al. 2004) Efforts to develop a novel NO donor for management of cardiovascular and pulmonary diseases assume a new and increased relevance to the need for experimental therapeutics in the COVID-19 pandemic.

Coeurative, Inc. expects that nitrate donors that contain urea or analogues of urea such as glycolamide will be of therapeutic value in delivering anti-viral NO to combat vascular endothelial dysfunction in the treatment of COVID-19, a disease characterized by systemic hypoxia and inflammation due to SARS-CoV-2 infection.

The papain-like protease (PLpro) was considered as a primary target for therapeutic inhibition of the first SARS-CoV. (Baez-Santos, St John et al. 2015) PLpro was judged to have a high affinity for ribavirin in an in silico study of SARS-CoV-2 and ribavirin was at first believed to be a potential therapeutic agent. (Wu, Liu et al. 2020) However, some of the compounds described herein appear to have a higher affinity as they sit firmly in the catalytic pocket of $PL^{pro}$ and makes the most of key interactions with the catalytic pocket residues: Leu162-Asp164 motif, Gly271-Tyr264 motif. These data call for a new focus on these novel antiviral agents as they appear to bind with increased avidity to PLpro and the ADP-ribose phosphatase of Nsp3 (compared with other known antivirals) while targeting delivery of NO to the SARS-CoV-2 virus in COVID-19.

SUMMARY OF THE INVENTION

Accordingly, in an aspect, the present invention provides novel methods for treating infectious diseases, comprising: administering to a mammal in need thereof a therapeutically effective amount of at least one of the compounds of the present invention or a pharmaceutically acceptable salt thereof.

In another aspect, the present invention provides novel pharmaceutical compositions, comprising: a pharmaceutically acceptable carrier and a therapeutically effective amount of at least one of the compounds of the present invention or a pharmaceutically acceptable salt thereof, wherein the composition is suitable for treating infectious diseases.

In another aspect, the present invention provides novel compounds or pharmaceutically acceptable salts for use in therapy.

In another aspect, the present invention provides the use of novel compounds for the manufacture of a medicament for the treatment of infectious diseases.

These and other objects, which will become apparent during the following detailed description, have been achieved by the inventor's discovery that the presently claimed compounds or pharmaceutically acceptable salts thereof are expected to provide a therapeutic response focused on the etiologic agents associated with infectious diseases.

BRIEF DESCRIPTION OF THE DRAWINGS

FIG. 1A is an overlay of the top hits and control compound in PLpro catalytic pocket: Leu162-Asp164 motif, Gly271-Tyr264 motif. FIG. 1B shows compound CR-0305. FIG. 1C shows compound CR-0607. FIG. 1D shows compound CR-0510. As seen in FIGS. 1B-D, compounds CR-0305, CR-0607, and CR-0510 were predicted to make key interactions to catalytic pocket residues.

FIG. 2A is an overlay of the top hits and control compound in ADP-ribose phosphatase catalytic site. FIG. 2B shows compound CR-0504. FIG. 2C shows compound CR-0502. FIG. 2D shows compound CR-0402. As seen in FIGS. 2B-D, compounds CR-0504, CR-0502, and CR-0402 were predicted to make key interactions to the binding pocket residues.

(FIG. 4C) and (FIG. 4D): The Root Mean Square Deviation (RMSD) is used to measure the average change in displacement of a selection of atoms for a particular frame with respect to a reference frame. Binding of CR-0305 (FIG. 4C) to the catalytic site of $PL^{pro}$ is more stable than binding of GRL-0617 (FIG. 4D) over time.

DETAILED DESCRIPTION OF THE INVENTION

Figure 1A:
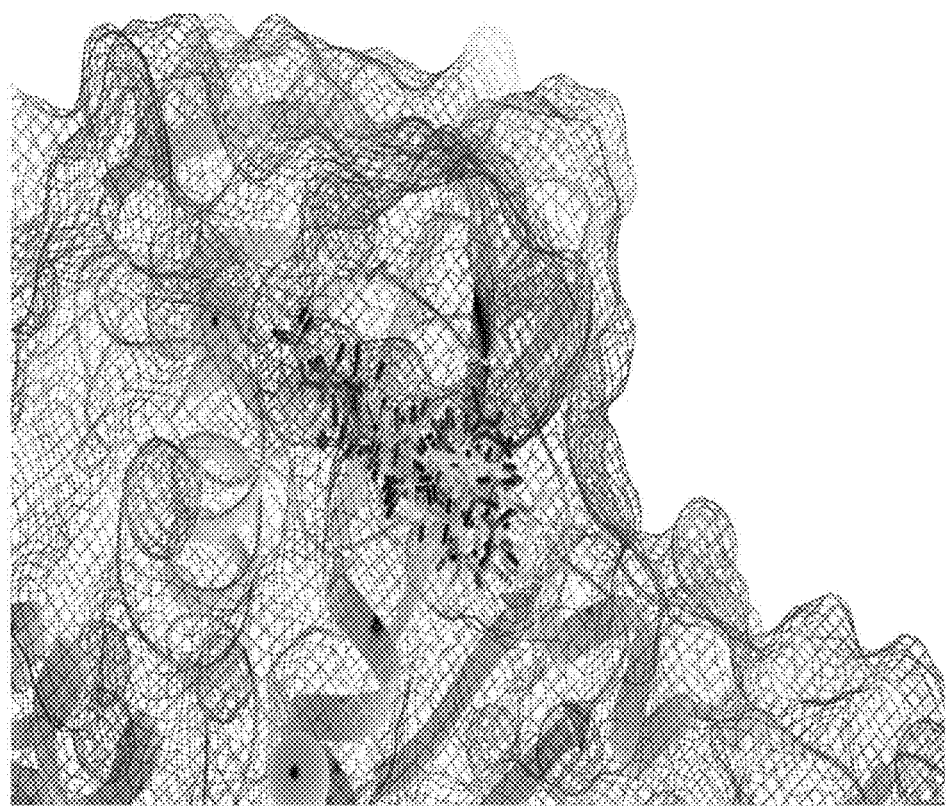
FIGS. 1A-D.
Figure 1B:
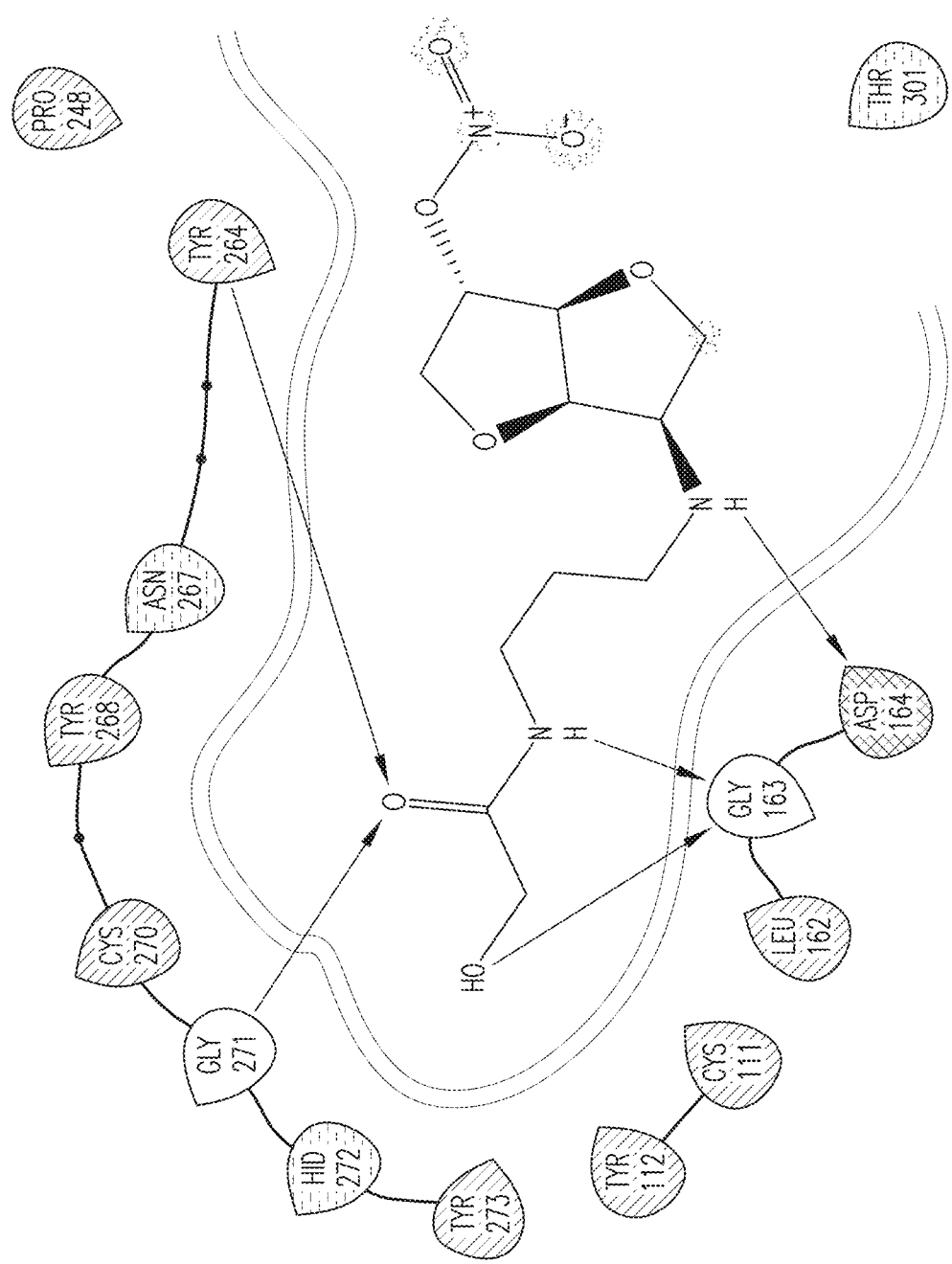
Figure 1C:
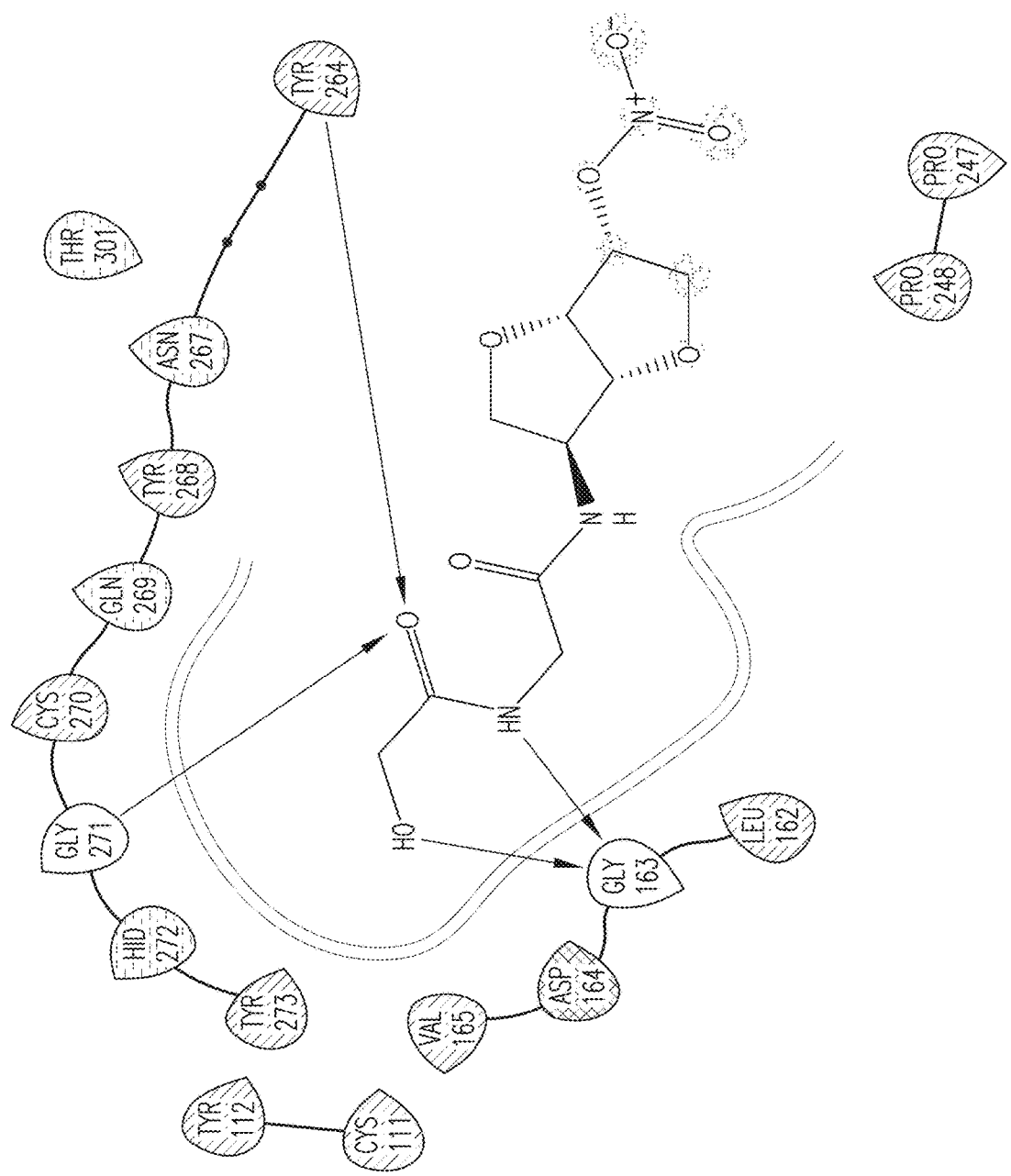
Figure 1D:
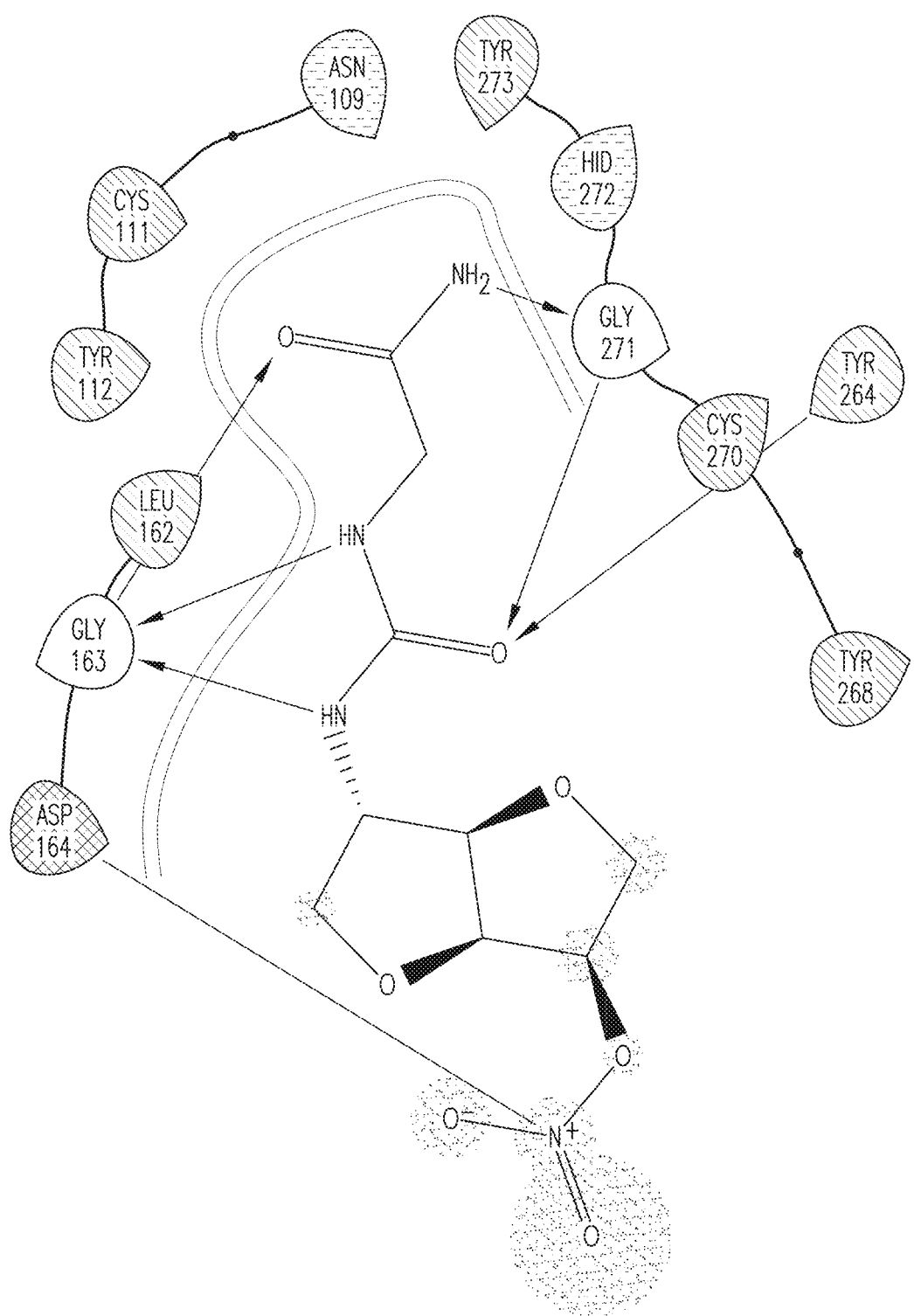
Figure 2A:
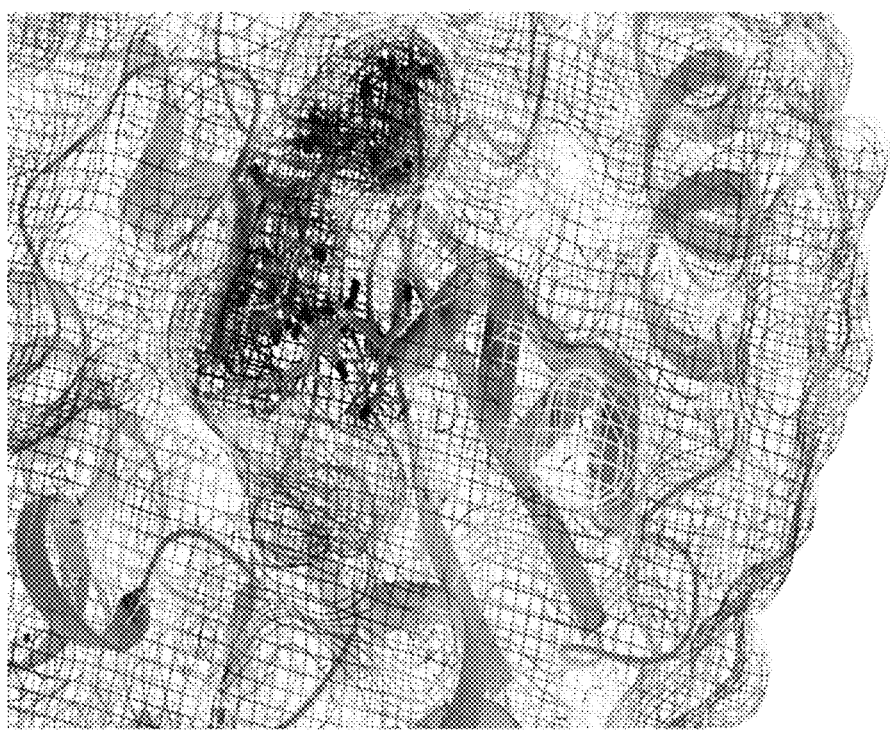
FIGS. 2A-D.
Figure 2B:
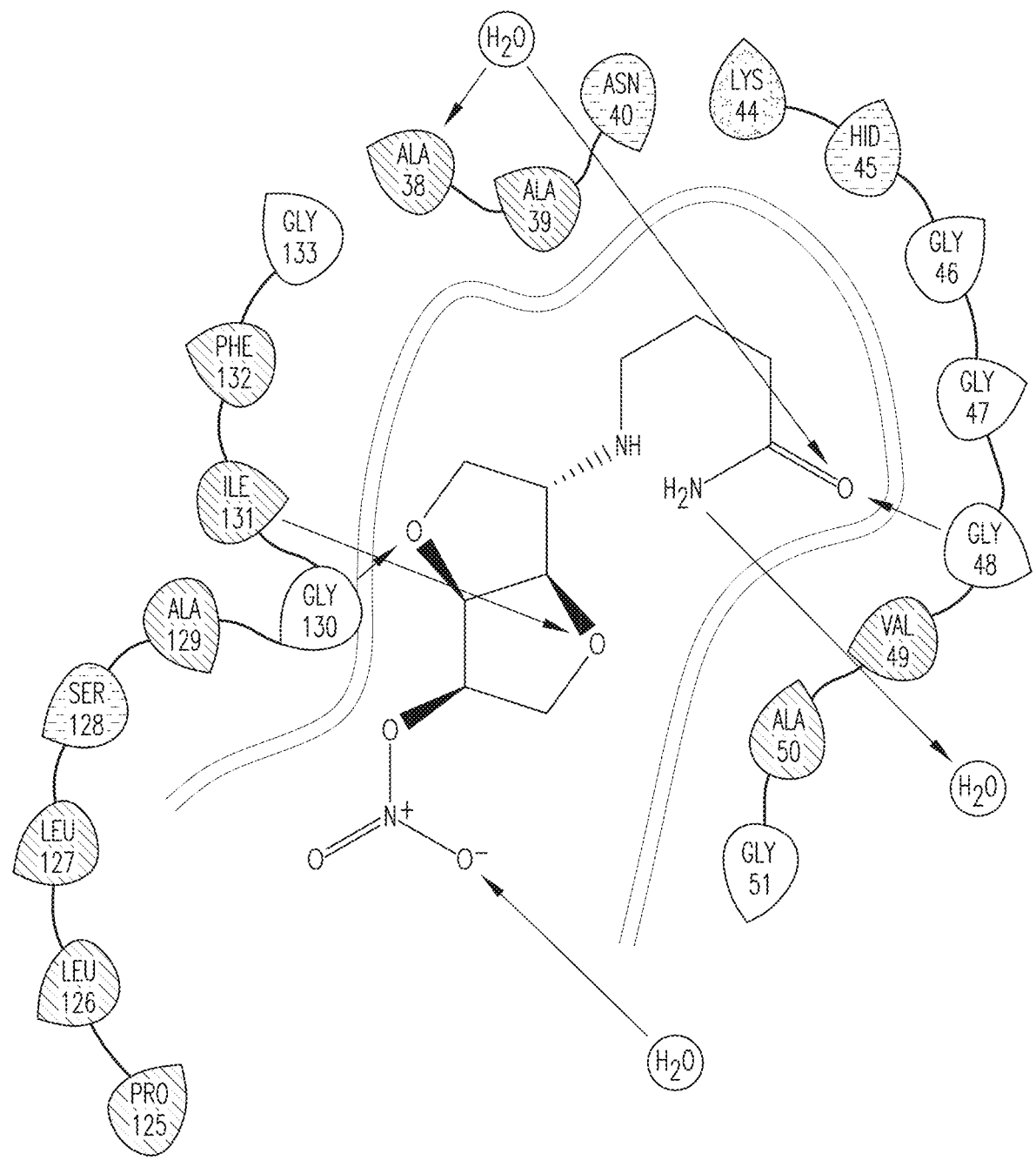
Figure 2C:
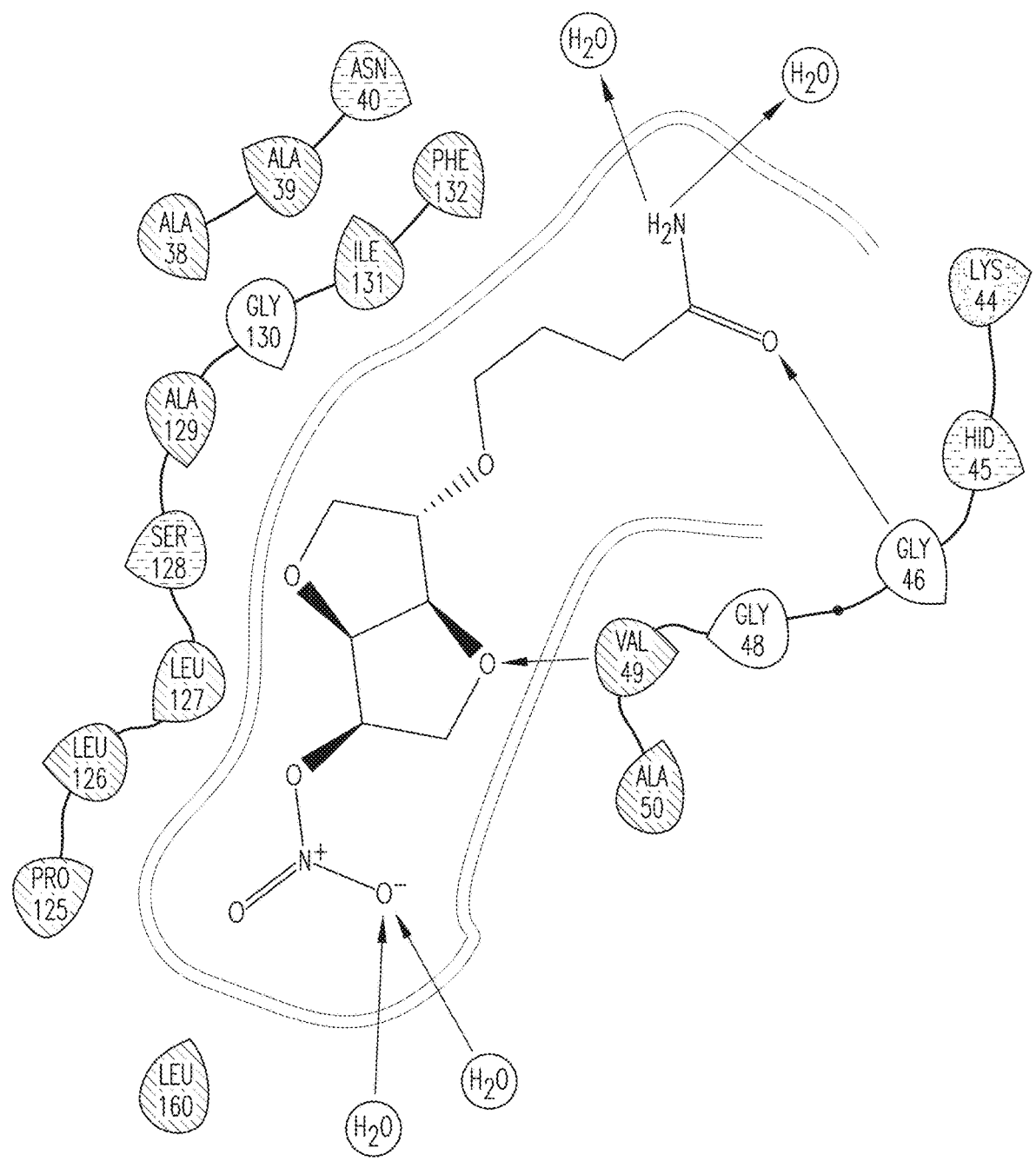
Figure 2D:
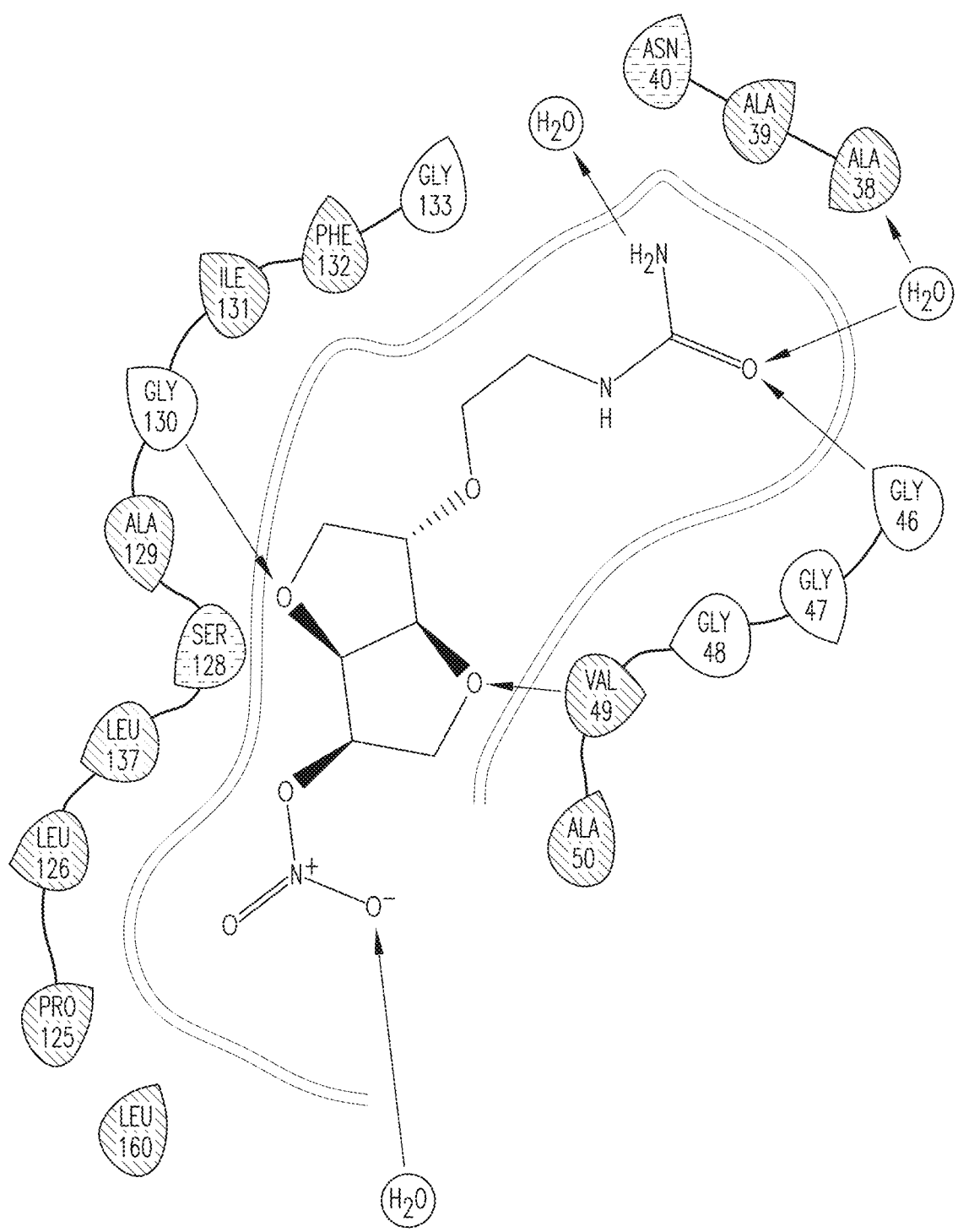

All references cited herein are hereby incorporated in their entirety herein by reference.

Since COVID-19 lung and heart complications create hypoxia, or a generalized state of low oxygen delivery to bodily organs, (Giustino, Pinney et al. 2020, Wiersinga, Rhodes et al. 2020) strategies to manage COVID-19 should optimize oxygen delivery. Vasodilatation is desired in the setting of oxygen deprivation as well as modulation of the secondary inflammatory responses associated with hypoxia. The compounds described herein were originally developed to manage tissue hypoxia due to cardiovascular disease. They were developed with the intention of using them for treatment of angina pectoris, related to coronary arterial insufficiency, with the additional hope that they would assist in ischemic preconditioning of vulnerable myocardium through events mediated by NO. But NO donors could also be of therapeutic value in delivering anti-viral NO to combat vascular endothelial dysfunction in the treatment of COVID-19, a disease characterized by systemic hypoxia and inflammation due to SARS-CoV-2 infection. Early reports on the cardiovascular and pulmonary impact of SARS-CoV-2 infection (Yang, Yu et al. 2020) provided practical evidence that NO could be beneficial. NO has antiviral activity by inhibiting viral proteases (Saura, Zaragoza et al. 1999) and there is inhibition of SARS-CoV infection in vitro by an NO donor. (Kevaerts, Vijgen et al. 2004) Inhaled NO has been shown to be of clinical benefit for COVID-19 patients with pulmonary hypertension. (Feng, Yang et al. 2020) NO donors have been shown to inhibit coxsackievirus B3 proteases in animal models of myocarditis and may have a broad applicability as antivirals. (Zell, Markgraf et al. 2004)

The compounds used herein were designed around previous observations regarding the expression of the gene SLC14A1, encoding Urea Transport Protein B (UT-B.) Intracellular urea concentrations are maintained by the action of UT-B and its active expulsion of urea across cell membranes. UT-B is expressed in the heart, vascular endothelium and erythrocytes. (Shavakul, Clemencon et al. 2013) SLC14A1 (RACH1) mRNA was markedly overexpressed in human vascular endothelial cells in culture under hypoxic (1% oxygen) conditions compared with normoxia (20%) in overexpression libraries derived from human vascular endothelium (HMEC-1) and this likely contributes to the previously documented reduction in eNOS-NO pathway activity in hypoxia. (Schmedtje, Ji et al. 1997) The mechanism for this interaction between eNOS and hypoxia was unclear until it was observed that intracellular accumulation of urea due to inhibition of UT-B leads to increased breakdown of arginine by nitric oxide synthase instead of arginase. Feedback inhibition of arginase can lead to increased eNOS activity via this alternate pathway of arginine metabolism. (Sun, Lau et al. 2016) Upregulation of expression of UT-B in hypoxia may lead to transport of urea out of the endothelial cell, and therefore a decrease in nitric oxide synthase activity, since the precursor arginine can be alternatively broken down by arginase to urea, and then expelled by UT-B. NO donors that contain urea or analogues of urea such as glycolamide (Zhao, Sonawane et al. 2007) might therefore be therapeutically useful in restoring eNOS activity while also directly donating NO.

Where tissue hypoxia is observed due to COVID-19 and/or vascular insufficiency, one wishes to potentiate vasodilatory release of NO, overcoming the reduction in eNOS observed in hypoxia. One might overcome the inhibition of eNOS associated with hypoxia by potentiating the formation of NO from arginine through feedback inhibition of the arginase pathway of arginine metabolism via an increase in local concentrations the product of arginase, urea, and analogues. The development of novel NO donors took on a new relevance with the need for novel experimental therapeutics the COVID-19 pandemic.

Subsequently, an examination in silico of the avidity of binding of these compounds to nine key SARS-CoV-2 targets revealed surprisingly stable and avid binding of the investigational compound CR-0305 (defined herein as formula III-compound 5, where $R^1=(CH_2)_3NH$) to the catalytic site of the key SARS-CoV-2 papain-like protease $PL^{pro}$, pointing to another potential therapeutic mechanism of action, particularly in the setting of cardiovascular complications. CR-0305 is an NO donor that, as an antianginal agent, could modulate inflammation and deliver vasodilatation in the setting of local hypoxia. The SARS-CoV-2 3CL hydrolase ($M^{pro}$) is an important target for antiviral drug therapy (Choudhary, Shaikh et al. 2020) but the papain-like protease ($PL^{pro}$) of SARS-CoV-2 is a primary target for therapeutic inhibition of the SARS viruses as it mediates viral replication and modulates host immune responses through attenuation of type 1 interferon responses. (Mantlo, Bukreyeva et al. 2020, McClain and Vabret 2020, Shin, Mukherjee et al. 2020) CR-0305 may act not only as an NO donor but also as a direct inhibitor of PL$^{pro}$. This dual effect should prove useful in control of the COVID-19 pandemic.

The proposed mechanism of action of CR-0305 in COVID-19 involves binding of CR-0305 to the protease PLpro at its catalytic site while using affinity to PLpro to target delivery of nitric oxide (NO) to SARS-CoV-2 in the form of the nitrate group attached to isosorbide at the 2-carbon. CR-0305 is superior to GRL-0617, Remdesivir, GS-441524, Lopinavir, Boceprevir and Ribavirin in binding PL$^{pro}$ based on in silico data. CR-0305 appears to have a higher affinity to SARS-CoV-2 than other antivirals as it sits firmly in the PL$^{pro}$ catalytic pocket and makes the most of critical interactions with the key catalytic pocket amino acids Gly163, Asp164, Gly271 and Tyr264. CR-0305 could prove superior to NO and other antivirals because, in silico, CR-305 binds to the catalytic site of PL$^{pro}$ to block protease activity essential for viral replication and inhibit interferon-based cellular defense mechanisms while targeting delivery of antiviral NO to the SARS-CoV-2 virus in COVID-19.

An infectious disease is a disease caused by at least one of a virus (viral infection), bacteria (bacterial infection), protozoa or helminth (parasitic infection), or fungus (fungal infection). The infectious disease is treatable by the compounds of the present invention because nitric oxide can be anti-viral (MacMicking, Xie et al. 1997, Zell, Markgraf et al. 2004) anti-bacterial(Yang, Feura et al. 2018), anti-parasitic (Muro and Perez-Arellano 2010, Yim, Park et al. 2018), and anti-fungal (Stasko, McHale et al. 2018) and the compounds of the present invention can function as nitric oxide donors.

Thus, in an aspect, the present invention provides a novel method for treating an infectious disease, comprising: administering to a patient in need thereof a therapeutically effective amount of at least one compound of the present invention or a pharmaceutically acceptable salt thereof.

In another aspect, the infectious disease is caused by a virus, bacterium, mycobacterium, parasite, fungi, or a combination thereof.

In another aspect, the infectious disease causes cellular hypoxia in the patient.

In another aspect, the patient is on a ventilator because of the infectious disease.

Examples of viruses (and viral infections) that can cause an infectious disease treatable by the present invention include coronaviruses (SARS-CoV (SARS), MERS-CoV (MERS), and SARS-CoV-2 (COVID-19), influenza types A, B, and C (flu), Vaccinia virus (smallpox), Herpes simplex virus-1 (herpes), Epstein-Barr virus (infectious cardiomyopathy), and, Coxsackie virus (infectious cardiomyopathy).

Examples of bacteria (and bacterial infections) that can be treatable by the present invention include *Streptococcus* (pneumonia and strep throat), *Escherichia coli* (urinary tract infection), *Serratia marcescens* (urinary tract infection), *Fusobacterium nucleatum* (periodontal disease), *Staphylococcus epidermidis* (sepsis), *Bacillus anthracis* (anthrax), *Pseudomonas aeruginosa* (pneumonia), *Klebsiella pneumoniae* (pneumonia), *Staphylococcus Aureus* including methicillin-resistant *S. aureus* MRSA (cellulits), *Listeria monocytogenes* (Listeriosis), *Clostridium difficile* (*C. difficile* infection), *Salmonella enterica* (salmonella), *Salmonella typhi* (typhoid fever) and *Clostridium perfringens* (clostridium food poisoning).

Examples of myco-bacteria and myco-bacterial infections that can be treatable by the present invention include *Mycobacterium tuberculosis* (tuberculosis), *Mycobacterium bovis* (bovine tuberculosis), *Mycobacterium avium* and *intracellulare* (MAC complex infection) and *Mycobacterium leprae* (Hansen's disease).

Examples of parasites and parasitic infections that can be treatable by the present invention include *Trypanosomiasis cruzi* (Chagas' disease), *Schistosoma mansoni* (schistosomiasis), *Toxoplasmosis gondii* (toxoplasmosis), *Plasmodium falciparum* (malaria), *Leishmania major* (leishmaniasis), *Acanthamoeba castellanii* (*Acanthamoeba keratitis*) and *Strongyloides stercoralis* (Loffler syndrome).

Examples of fungi and fungal infections that can be treatable by the present invention include *Tinea corporis* (dermatophytosis) and *Candida albicans* (candidiasis).

In another aspect, the compound to be administered is a novel compound of formula I, II, III, IV, V or VI:

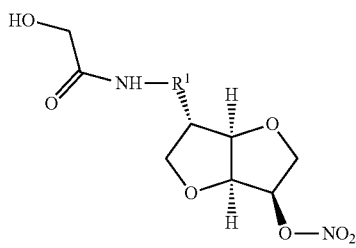

VI wherein:
R¹ is absent;
alternatively, R¹ is selected from (the right-hand portion of R¹ being attached to the isosorbide moiety): (CH₂)₂O, (CH₂)₂NH, (CH₂)₃O, (CH₂)₃NH, CH₂C(=O)O, and CH₂C(=O)NH; and,
R² is selected from (the right-hand portion of R² being attached to the isosorbide moiety): (CH₂)₂O, (CH₂)₂NH, (CH₂)₃O, (CH₂)₃NH, CH₂C(=O)O, CH₂C(=O)NH, CH₂OC(=O)O, CH₂OC(=O)NH, CH₂NHC(=O)O, and CH₂NHC(=O)NH;
or a pharmaceutically acceptable salt thereof.

In another aspect, the compound is of formula I or IV or a pharmaceutically acceptable salt thereof.

In another aspect, the compound is of formula I or IV and R¹ is absent or a pharmaceutically acceptable salt thereof.

In another aspect, the compound is of formula I or IV and R¹ is selected from: (CH₂)₂O (CH2)₂NH, (CH₂)₃O, and (CH₂)₃NH or a pharmaceutically acceptable salt thereof.

In another aspect, the compound is of formula II or V or a pharmaceutically acceptable salt thereof.

In another aspect, the compound is of formula II or V and R² is selected from: (CH₂)₂O (CH₂)₂NH, (CH₂)₃O, (CH₂)₃NH, CH₂OC(=O)O, CH₂OC(=O)NH, CH₂NHC(=O)O, and CH₂NHC(=O)NH or a pharmaceutically acceptable salt thereof.

In another aspect, the compound is of formula III or VI or a pharmaceutically acceptable salt thereof.

In another aspect, the compound is of formula III or VI and R¹ is absent or a pharmaceutically acceptable salt thereof.

In another aspect, the compound is of formula III or VI and R¹ is selected from: (CH₂)₂O (CH₂)₂NH, (CH₂)₃O, and (CH₂)₃NH or a pharmaceutically acceptable salt thereof.

In another aspect, the present invention provides novel pharmaceutical compositions, comprising: a pharmaceutically acceptable carrier and a therapeutically effective amount of a compound of the present invention or a pharmaceutically acceptable salt thereof.

In another aspect, the present invention provides a compound of the present invention for use in therapy.

In another aspect, the present invention provides the use of the present invention for the manufacture of a medicament for the treatment of infectious diseases.

The present invention may be embodied in other specific forms without departing from the spirit or essential attributes thereof This invention encompasses all combinations of aspects of the invention noted herein. It is understood that any and all embodiments of the present invention may be taken in conjunction with any other embodiment or embodiments to describe additional embodiments. It is also to be understood that each individual element of the embodiments is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

Cellular hypoxia is a lack of oxygen at the level of individual cells, not necessarily related to a lack of oxygen at the level of a whole organism or an environment.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Mammal" and "patient" cover warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic and organic acids selected from 1, 2-ethanedisulfonic, 2-acetoxybenzoic, 2-hydroxyethane-sulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycolylarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are useful. Lists of suitable salts are found in the Remington Pharmacy textbook (Gaisford 2021) the disclosure of which is hereby incorporated by reference.

"Therapeutically effective amount" includes an amount of a compound of the present invention that is effective when administered alone or in combination to treat the indication listed herein. "Therapeutically effective amount" also includes an amount of the combination of compounds claimed that is effective to treat the desired indication. The combination of compounds can be a synergistic combination. Synergy as described (Chou and Talalay 1984) occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Compounds of the present invention are expected to be active as described herein.

Formulations and Dosages

In the present invention, the compound(s) of the present invention can be administered in any convenient manner (e.g., enterally or parenterally). Examples of methods of administration include orally and transdermally. One skilled in this art is aware that the routes of administering the compounds of the present invention may vary significantly. In addition to other oral administrations, sustained release compositions may be favored. Other acceptable routes may include injections (e.g., intravenous, intramuscular, subcutaneous, and intraperitoneal), subdermal implants, buccal, sublingual, topical, rectal, vaginal, and intra-airway administrations (e.g., via inhalation). Examples of oral formulations include tablets, coated tablets, hard and soft gelatin capsules, solutions, emulsions, suspensions, and aerosolizable compositions. Bioerodible, non-bioerodible, biodegradable, and non-biodegradable systems of administration may also be used, including drug-eluting structures such as stents, placed by catheter, that may deliver the present compounds directly to a vessel wall.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is typically calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example $\alpha$-, $\beta$-, or $\gamma$-cyclodextrin, 2-hydroxypropyl-$\beta$-cyclodextrin, and/or methyl-$\beta$-cyclodextrin.

The dose of the compound of the present invention administered daily will vary on an individual basis and to some extent may be determined by the severity of the disease being treated. The dose of the compound of the present invention will also vary depending on the compound administered. Examples of dosages of compounds of the present invention include from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The compound can be administered in a single dose or in a number of smaller doses over a period of time. The length of time during which the compound is administered varies on an individual basis, and can continue until the desired results are achieved. Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
| --- | --- |
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Capsule |
| --- | --- |
| Active ingredient | 50 |
| Crystalline lactose | 60 |
| Microcrystalline cellulose | 39 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the magnesium stearate is admixed. The final mixture is filled into hard gelatin capsules of suitable size.

A possible example of an injection solution of the present invention is as follows.

| Ingredient | mg/Solution |
| --- | --- |
| Active substance | 1.0 mg |
| 1N HCl | 20.0 μl |
| acetic acid | 0.5 mg |
| NaCl | 8.0 mg |
| Phenol | 10.0 mg |
| 1N NaOH | q.s. ad pH 5 |
| H₂O | q.s. ad 1 mL |

A possible example of a topical composition of the present invention is as follows.

| Ingredient | mg/dosage |
| --- | --- |
| Active ingredient | 2 |
| Dimethyl sulfoxide | 45 |
| Ethanol | 25 |
| Propylene glycol | 10 |
| Water | 18 |

A possible example of an aerosol formulation of the present invention is as follows (e.g., to be used with a nebulizer).

| Ingredient | mg/dosage |
| --- | --- |
| Active ingredient | 2 |
| Benzyl alkonium chloride | 0.01 |
| EDTA | 0.05 |
| Water | ~98 (to 100 mg) |

Other features of the invention will become apparent in the course of the following descriptions of exemplary embodiments that are given for illustration of the invention and are not intended to be limiting thereof.

Synthesis Examples

The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is found in *Protective Groups In Organic Synthesis*. (Greene and Wuts 1991) All references cited herein are hereby incorporated in their entirety herein by reference.

Synthesis Examples 1-34 are representative of the procedures that can be used to prepare compounds of the present invention. Synthesis examples 1-17 employ known compounds isosorbide-2-mononitrate (5-hydroxy-1,4:3,6-dianhydro-D-glucitol 2-nitrate) and 5-amino-isosorbide-2-mononitrate (5-amino-1,4:3,6-dianhydro-D-glucitol 2-nitrate) and synthesis examples 18-34 employ isosorbide-5-mononitrate (2-hydroxy-1,4:3,6-dianhydro-D-glucitol 5-nitrate) and 2-amino-isosorbide-5-mononitrate (2-amino-1,4:3,6-dianhydro-D-glucitol 5-nitrate) as starting materials. The synthesis examples 1-17 are for formulas I, II and III and synthesis examples 18-34 are for formula IV, V and VI in the Detailed Description of the Invention.

Synthesis Example 1

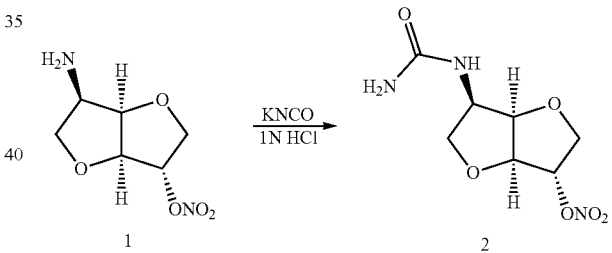

5-Amino-isosorbide-2-mononitrate (1) 1N HCl solution can be treated with potassium isocyanate at room temperature with stirring for 10-12 hours to afford the 2-ureido derivative (2) upon conventional work-up via extraction.

Synthesis Example 2

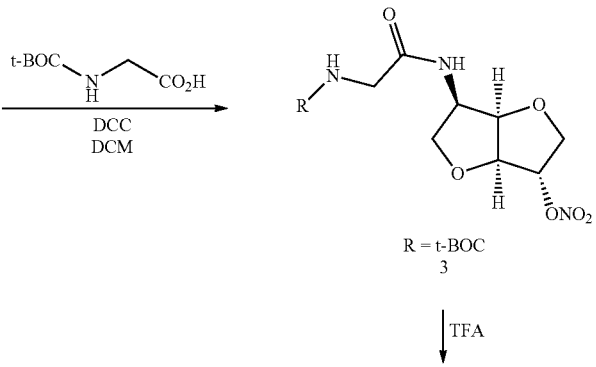

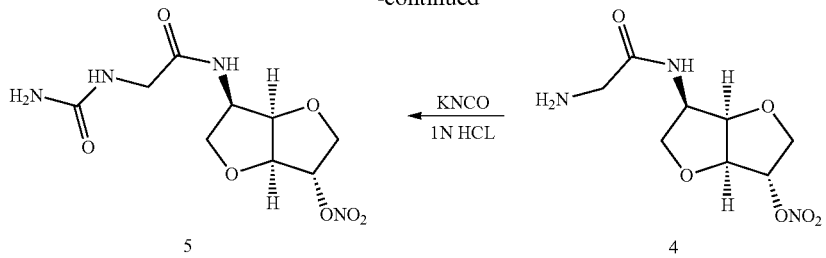

5-Amino-isosorbide-2-mononitrate (1) can be treated with N-t-BOC-glycine (t-BOC=tertiary butyl-oxycarbonyl) in dichloromethane in the presence of N,N'-dicyclohexyl-carbodiimide (DCC) and dimethyl-aminopyridine (DMAP). After overnight stirring at ambient temperature, the t-BOC amide (3) can be isolated in the conventional manner. Subsequent treatment of (3) with trifluoroacetic acid can provide the de-protected amino acid adduct (4) which upon treatment with potassium isocyanate and dilute HCl solution as previously described can afford the ureido glycine adduct (5).

Synthesis Example 3

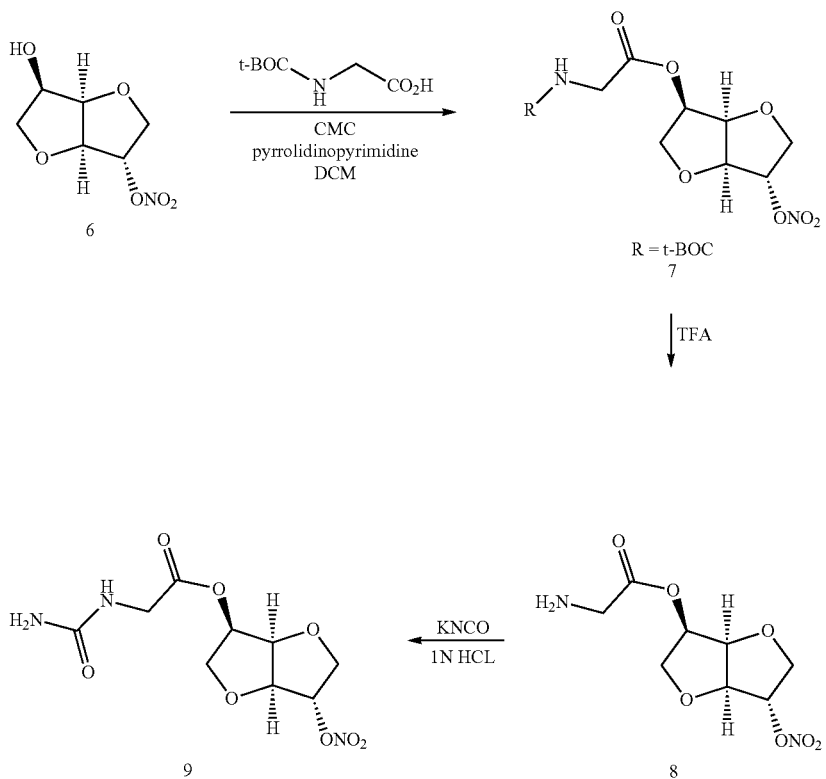

Treatment of isosorbide-2-mononitrate (6) in dichloromethane (DCM) with 1-cyclohexyl-3-(2-morpholinyl)carbodiimide (CMC) in the presence of pyrrolidinopyrimidine can afford the protected amino acid addict (7). Removal of the protecting group with TFA (trifluoro-acetic acetate) can provide the amino compound (8). Subsequent treatment with potassium isocyanate and dilute HCl solution at 0° C. to ambient temperature can yield the urea compound (9).

Synthesis Example 4

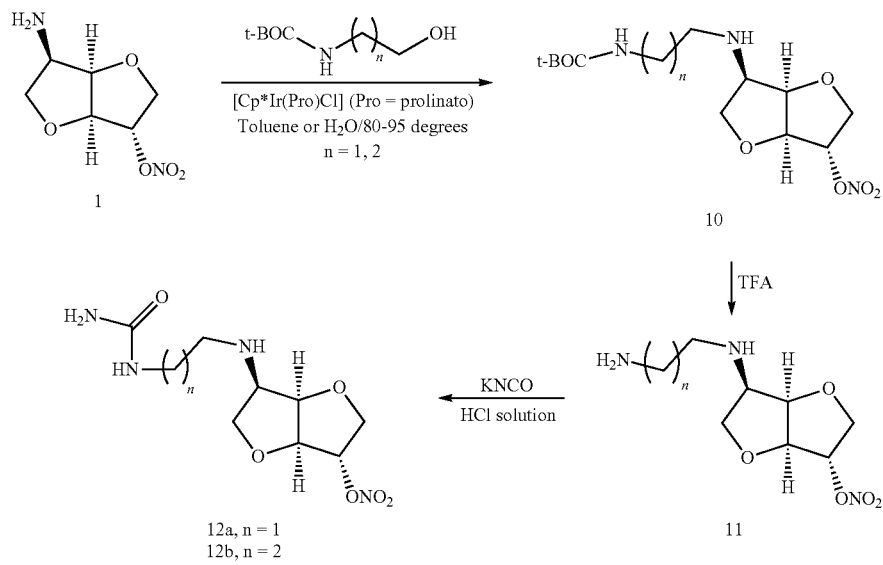

Treatment of 5-amino-isosorbide-2-mononitrate (1) with t-BOC-amino ethanol or t-BOC-3-aminopropanol in toluene or water in the presence of [Cp*Ir(Pro)Cl] (Pro=prolinato) (Cp=cyclopentadienyl) can afford the protected diamino adducts (10). Removal of the protecting group with TFA can afford the primary amines (11), which can be converted to the ureas (12a, 12b) using potassium cyanate in dilute hydrochloric acid solution, as previously described.

Synthesis Example 5

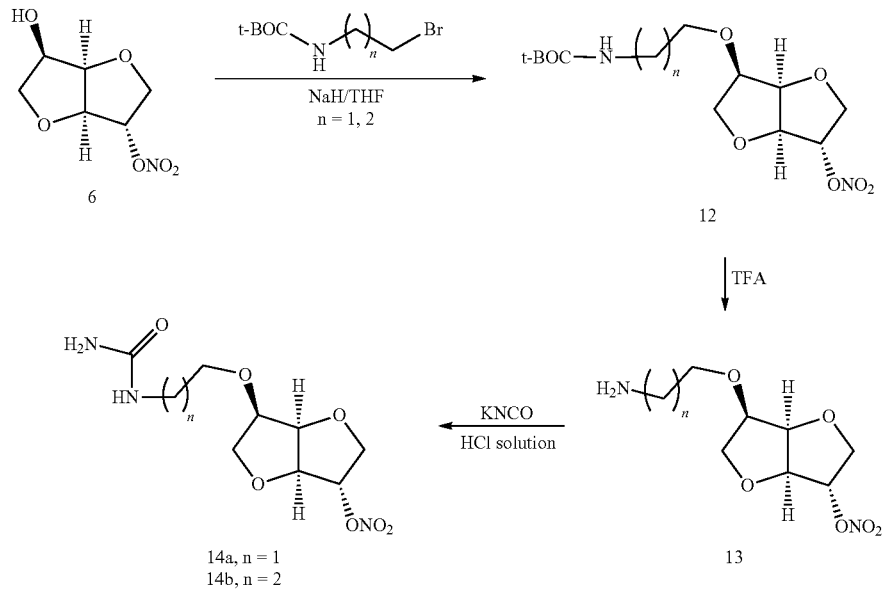

Isosorbide-2-mononitrate (6) can be deprotonated with sodium hydride or lithium di-isopropyl amide in tetrahydrofuran (THF) and then treated with with t-BOC-amino ethyl bromide or t-BOC-3-aminopropyl bromide to give the ethers (12). Deprotection of the t-BOC group using TFA will give the primary amine (13) and subsequent treatment potassium isocyanate as previously described can give the ureas (14).

Synthesis Example 6

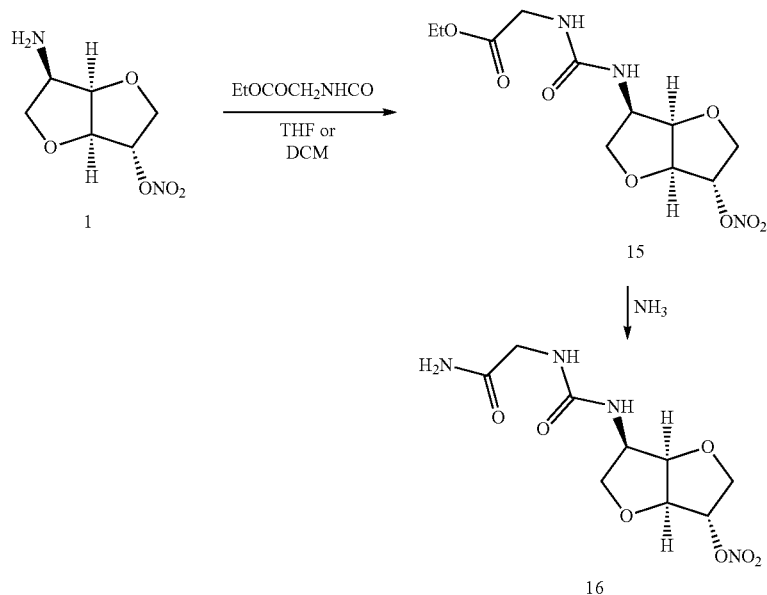

Treatment of 5-amino-isosorbide-2-mononitrate (1) with ethylcyananoacetate in THF or DCM can yield the urea (15). Further reaction with anhydrous ammonia in methanol can produce the ureido carboxamide (16).

Synthesis Example 7

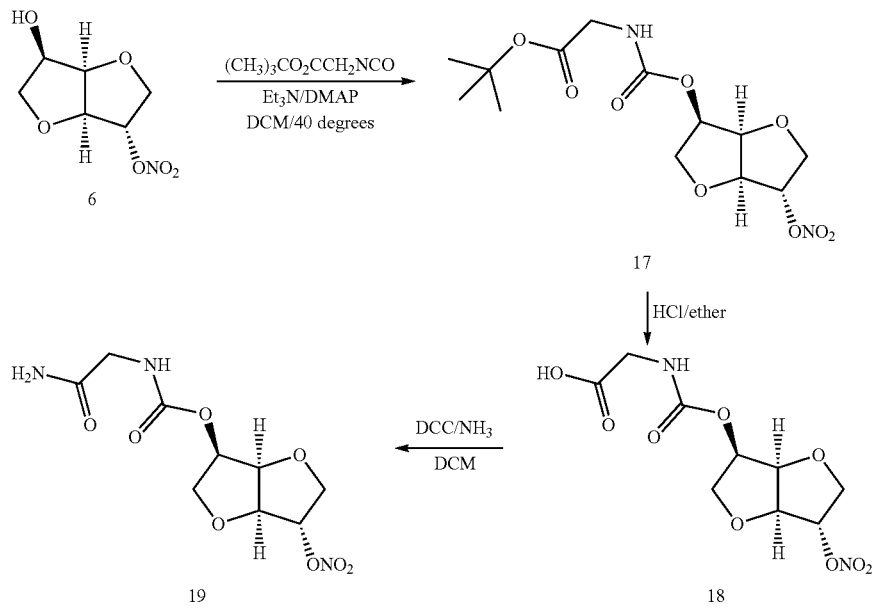

Treatment of isosorbide-2-mononitrate (6) with t-butyl-cyanoacetate in acetonitrile in the presence of N-methyl imidazole can yield the carbamate (17). Removal of the t-butyl group can be achieved with HCl in ether or with TFA to give the carboxylic acid (18). Amidation of the acid with ammonia in the presence of DCC can provide the carboxamide (19).

Synthesis Example 8

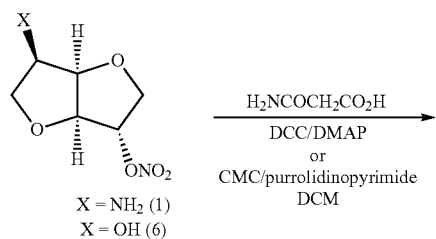

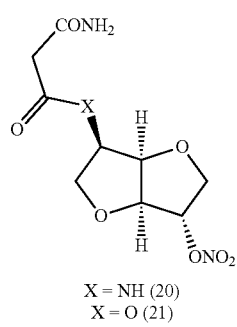

Treatment of 5-amino-isosorbide-2-mononitrate (1) or isosorbide-2-mononitrate (6) with malonic acid monoamide in DCM in the presence of DCC/DMAP or CMC/pyrrolidinopyrimidine can produce the malonamide (20) or the malono-ester-amido (21), respectively.

Synthesis Example 9

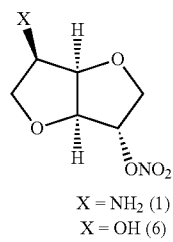

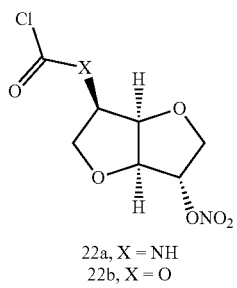

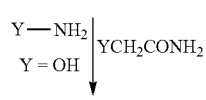

X = NH (20)
X = O (21)

22a, X = NH
22b, X = O

Y—NH$_2$
Y = OH  | YCH$_2$CONH$_2$

-continued

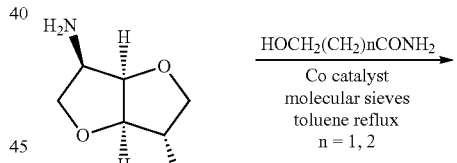

X = NH Y = NH (23)
X = NH, Y = O (24)
X = O, Y = NH (25)
X = O, Y = O (26)

Treatment of 5-amino-isosorbide-2-mononitrate (1) with phosgene and pyridine at about 0° C. can produce the carbamoyl chloride (22a, X=NH). Reaction of this carbamoyl chloride with glycinamide at low temperatures in the presence of DMAP in DCM can afford the ureido carboxamide (23). Alternatively, the carbamoyl chloride (22) (X=NH) can be treated with glycolamide in the presence of DMAP in DCM and to afford the carbonate with the terminal carboxamide group (24). If isosorbide-2-mononitrate (6) is used as the starting material for this sequence, the phosgene reaction can produce the carbonyl chloride at low temperature (22, X=O) and if this intermediate is treated with glycinamide or glycolamide under the conditions previously described, the carbamate (25) or the carbonate (26), respectively, can be prepared.

Synthesis Example 10

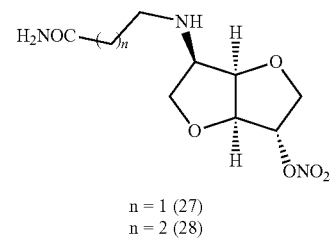

n = 1 (27)
n = 2 (28)

Treatment of 5-amino-isosorbide-2-mononitrate (1) with 3-hydroxypropionamide or 4-hydroxy butanamide in the presence of cobalt catalyst and molecular sieves in toluene at elevated temperatures can produce the carboxamidoamines (27) and (28), respectively.

Synthesis Example 11

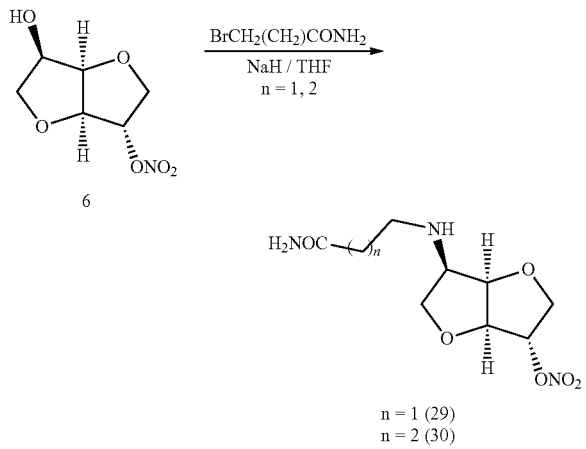

Treatment of isosorbide-2-mononitrate (6) with sodium hydride in THF or lithium diisopropylamide in THF and subsequent alkylation of the alkoxide with 3-bromoprionamide or 4-bromobutanamide can yield the carboxamido-ethers (29) and (30), respectively.

Synthesis Example 12

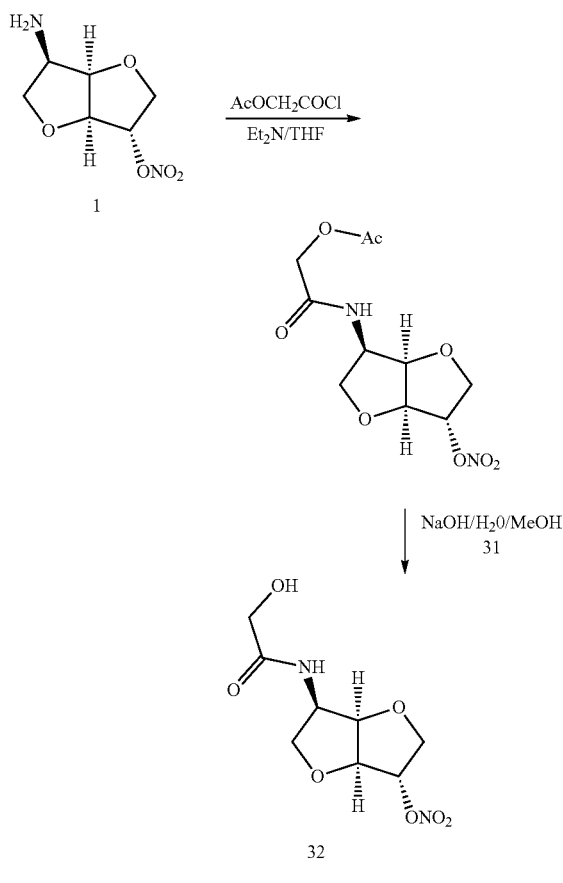

Treatment of 2-amino-isosorbide-5-mononitrate (1) with acetoxyacetyl chloride in the presence of triethylamine in THF can produce the amide adduct (31). Hydrolysis of the acetate with sodium hydroxide solution can produce the hydroxyl amide (32).

Synthesis Example 13

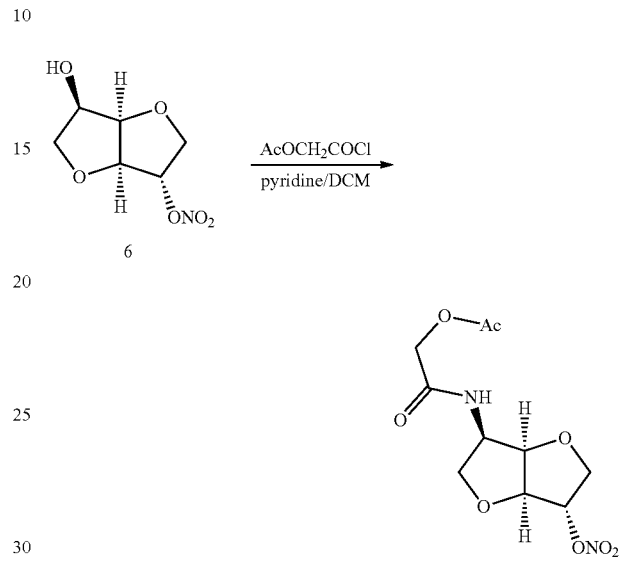

Treatment of isosorbide-2-mononitrate (6) with acetoxyacetyl chloride in the presence of triethylamine in THF can produce the ester adduct (33). Hydrolysis of the acetate with dibutyl tin oxide will produce the glycolic acid adduct (34).

Synthesis Example 14

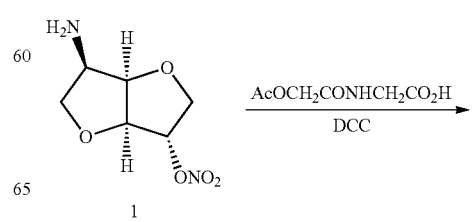

23                                                              24

-continued                                              Synthesis Example 15

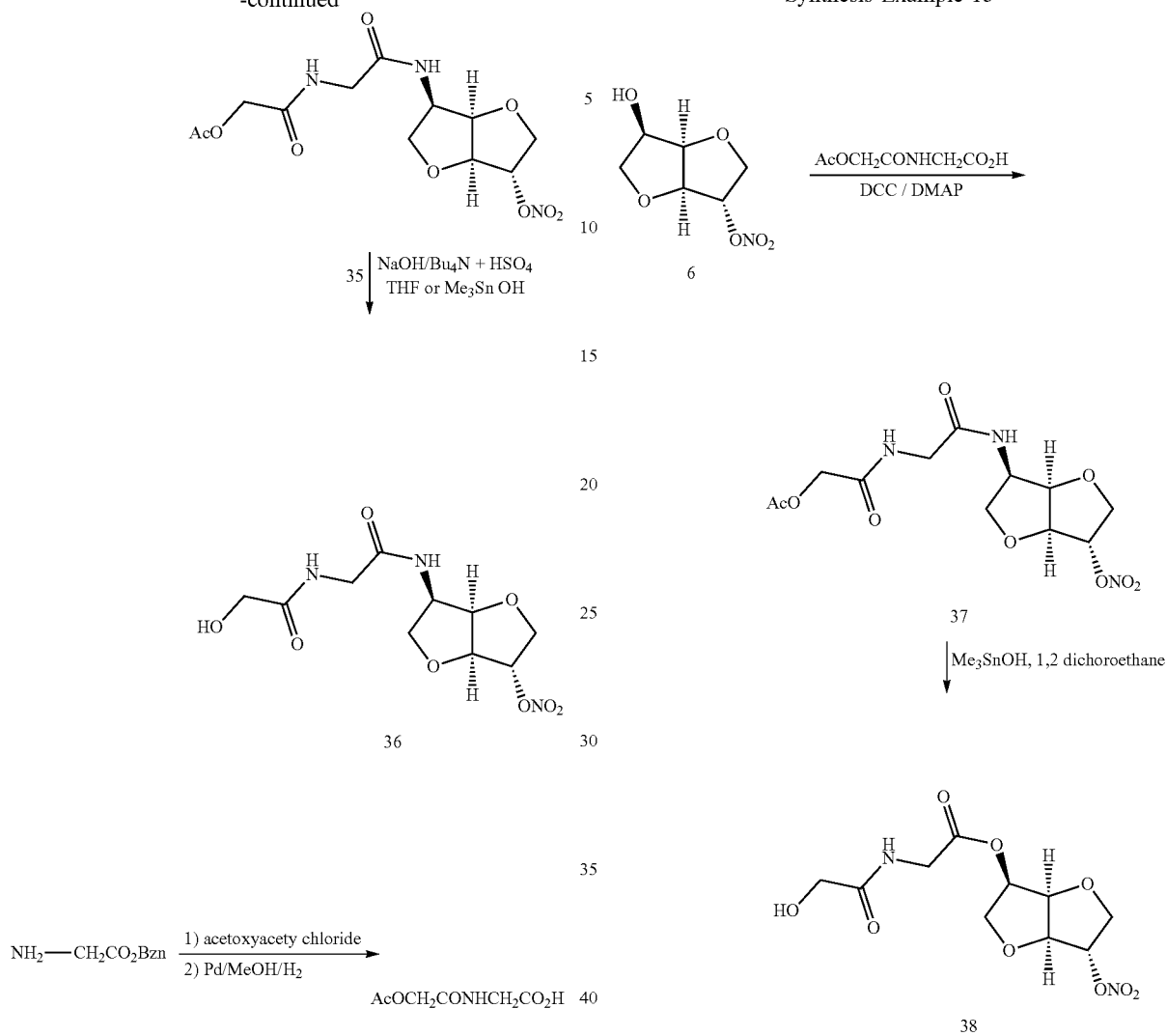

The N-acetoxyacetylglycine can be prepared by treatment of benzyl glycine with acetoxyacetyl chloride in the presence of triethylamine, followed by hydrogenolysis of the benzyl ester in the presence of palladium catalyst. Treatment of 5-amino-isosorbide-2-mononitrate (1) with acetoxy acetyl glycine in DCM in the presence of DCC can produce the acetylated amide adduct (35). Removal of the acetate (36) can be accomplished by reaction with KOH in methanol solution or with trimethyl tin hydroxide.

Treatment of isosorbide-2-mononitrate (6) with acetoxy acetyl glycine in DCM in the presence of DCC/DMP can produce the acetylated ester adduct (37). Removal of the acetate (38) can be accomplished by reaction with trimethyl tin hydroxide.

Synthesis Example 16

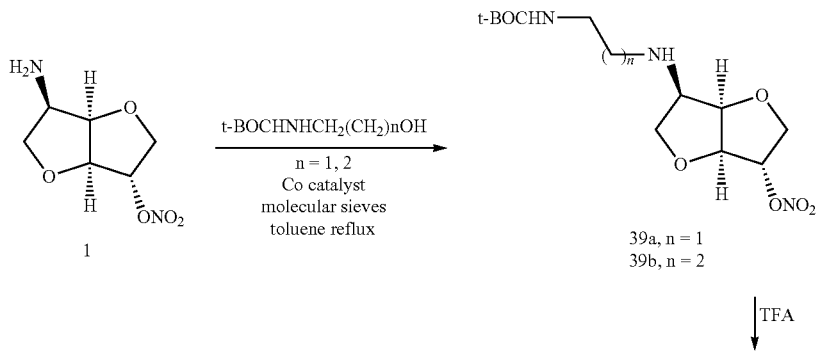

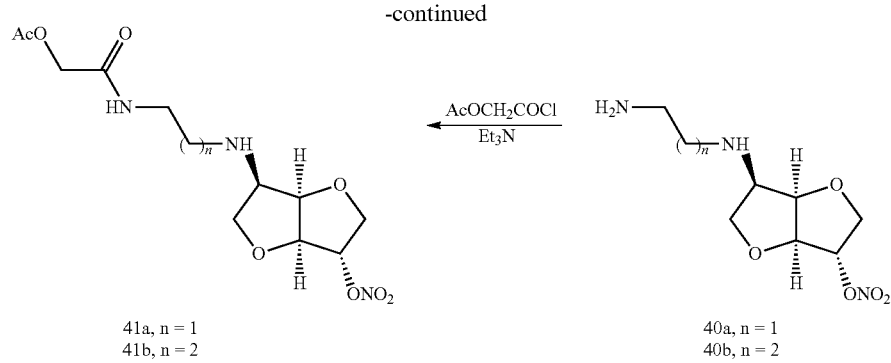

41a, n = 1
41b, n = 2

40a, n = 1
40b, n = 2

KOH/MeOH

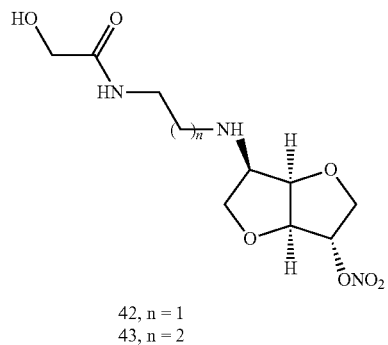

42, n = 1
43, n = 2

Treatment of 5-amino-isosorbide-2-mononitrate (1) with N-t-BOC-aminoethanol or N-t-BOC-3-aminopropanol in the presence of cobalt catalyst and molecular sieves in toluene at elevated temperatures can provide the protected amino compounds (39). Removal of the protecting group can be accomplished using TFA, which can give the unprotected primary amines (40). Reaction of the amines (40) with acetoxyacetyl chloride in the presence of trimethylamine can provide the amides (41), and subsequent treatment with KOH in methanol can afford the hydroxyacetamides (42 and 43).

Synthesis Example 17

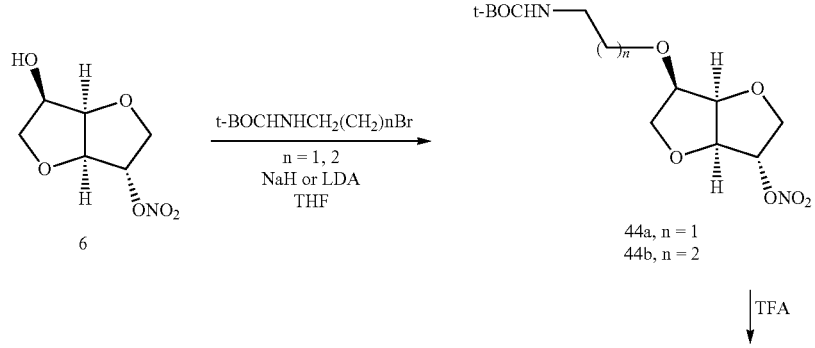

44a, n = 1
44b, n = 2

TFA

-continued

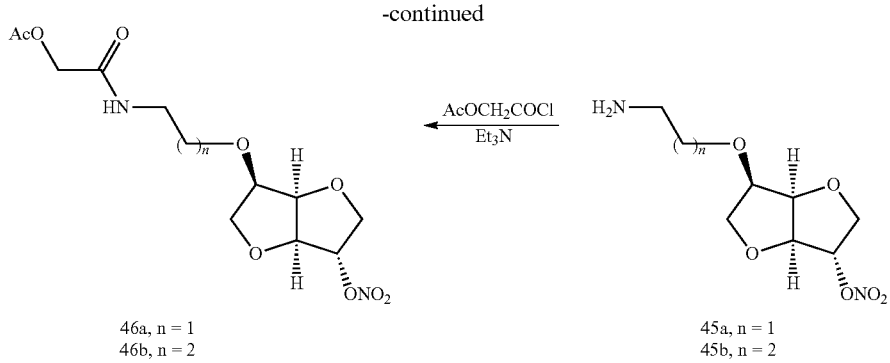

46a, n = 1
46b, n = 2

45a, n = 1
45b, n = 2

KOH/MeOH

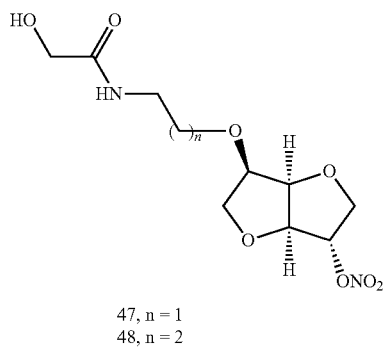

47, n = 1
48, n = 2

Deprotonation of isosorbide-2-mononitrate (6) with sodium hydride or LDA in THF followed by the addition of N-t-BOC-aminoethyl bromide or N-t-BOC-3-aminopropyl bromide can give the protected ethers (44). Deprotection of the amino groups using TFA can give the primary amines (45), which upon treatment with acteoxyacetyl chloride can give the amides (46). Hydrolysis of the acetate using KOH in MeOH can afford the hydroxacetamides (47 and 48).

Synthesis Example 18

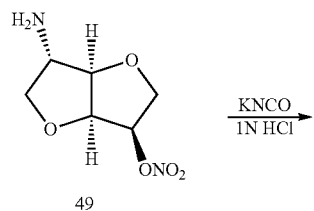

49

-continued

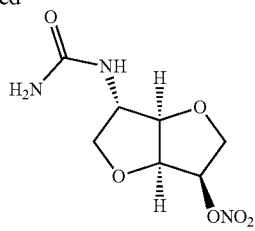

50

2-Amino-isosorbide-5-mononitrate (49) 1N HCl solution can be treated with potassium isocyanate at room temperature with stirring for 10-12 hours to afford the 2-ureido derivative (50) upon conventional work-up via extraction.

Synthesis Example 19

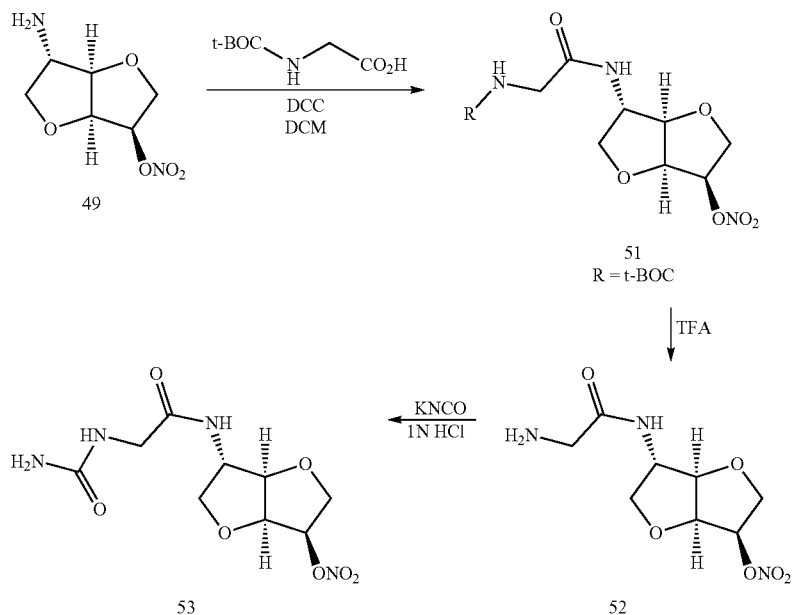

2-Amino-isosorbide-5-mononitrate (49) can be treated with N-t-BOC-glycine (t-BOC=tertiary butyl-oxycarbonyl) in dichloromethane in the presence of N,N'-dicyclohexyl-carbodiimide (DCC) and dimethyl-aminopyridine (DMAP). After overnight stirring at ambient temperature, the t-BOC amide (51) can be isolated in the conventional manner. Subsequent treatment of (51) with trifluoroacetic acid can provide the de-protected amino acid adduct (52) which upon treatment with potassium isocyanate and dilute HCl solution as previously described can afford the ureido glycine adduct (53).

Synthesis Example 20

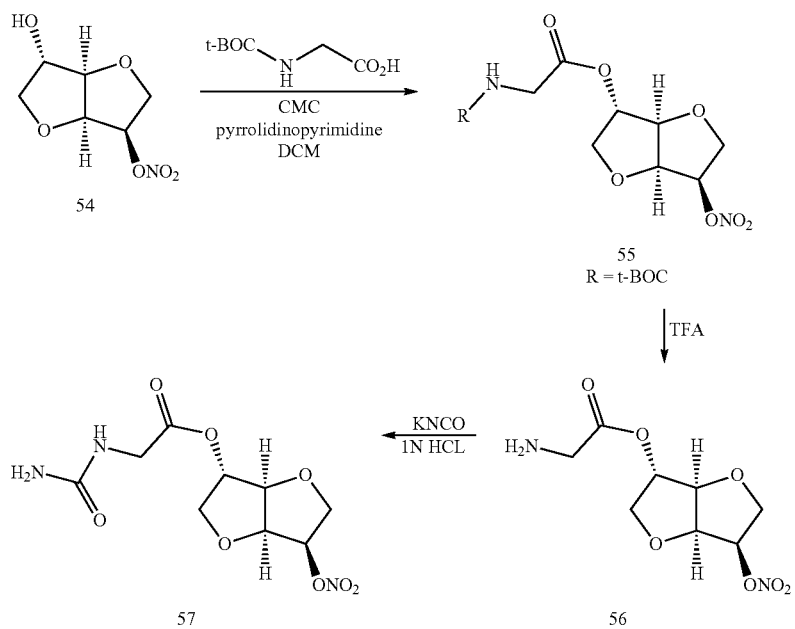

Treatment of isosorbide-5-mononitrate (54) in dichloromethane (DCM) with 1-cyclohexyl-3-(2-morpholinyl)carbodiimide (CMC) in the presence of pyrrolidinopyrimidine can afford the protected amino acid addict (55). Removal of the protecting group with TFA (trifluoro-acetic acetate) can provide the amino compound (56). Subsequent treatment with potassium isocyanate and dilute HCl solution at 0° C. to ambient temperature can yield the urea compound (57).

Synthesis Example 21

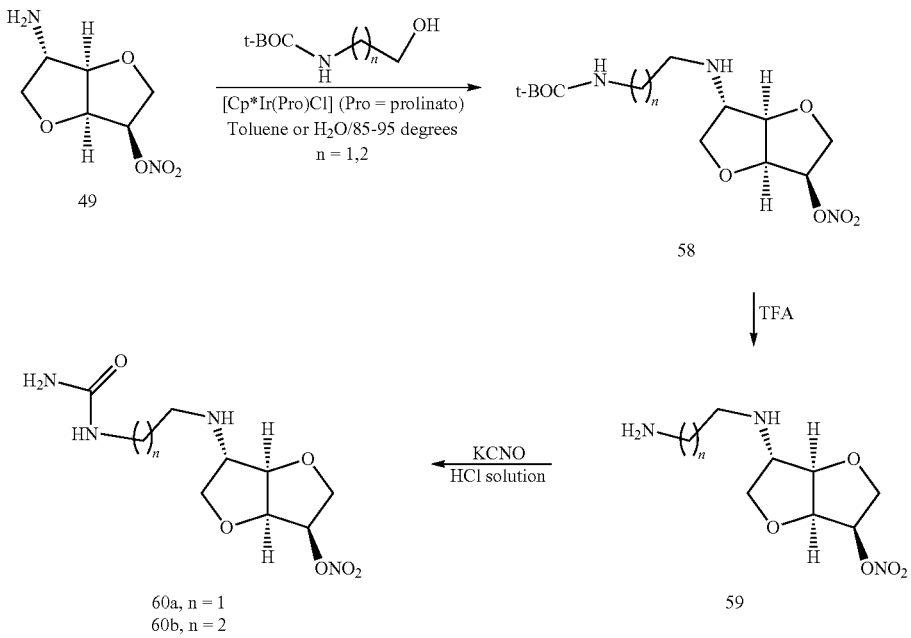

Treatment of 2-amino-isosorbide-5-mononitrate (49) with t-BOC-amino ethanol or t-BOC-3-aminopropanol in toluene or water in the presence of [Cp*Ir(Pro)Cl] (Pro=prolinato) (Cp=cyclopentadienyl) can afford the protected diamino adducts (58). Removal of the protecting group with TFA can afford the primary amines (59), which can be converted to the ureas (60a, 60b) using potassium cyanate in dilute hydrochloric acid solution, as previously described.

Synthesis Example 22

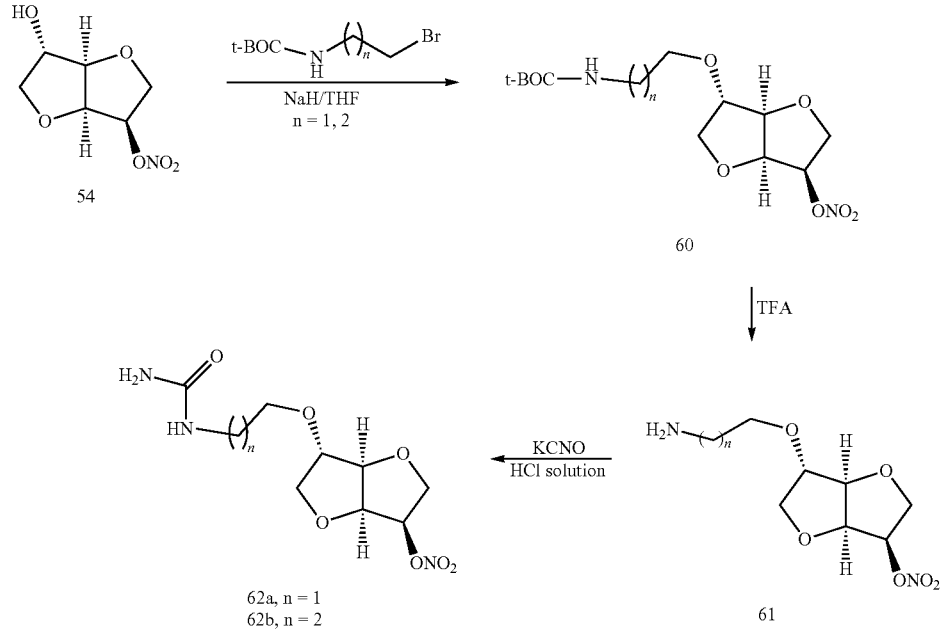

Isosorbide-5-mononitrate (54) can be deprotonated with sodium hydride or lithium di-isopropyl amide in tetrahydrofuran (THF) and then treated with with t-BOC-amino ethyl bromide or t-BOC-3-aminopropyl bromide to give the ethers (60). Deprotection of the t-BOC group using TFA will give the primary amine (61) and subsequent treatment potassium isocyanate as previously described can give theureas (62).

Synthesis Example 23

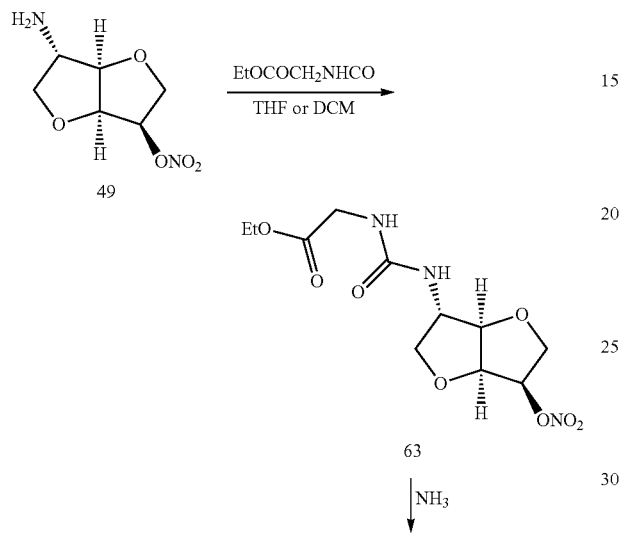

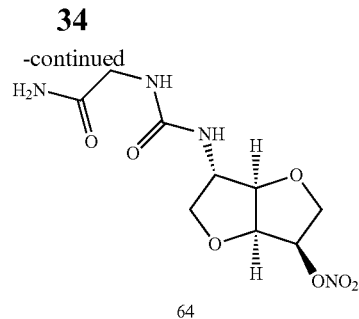

Treatment of 2-amino-isosorbide-5-mononitrate (49) with ethylcyananoacetate in THE or DCM can yield the urea (63). Further reaction with anhydrous ammonia in methanol can produce the ureido carboxamide (64).

Synthesis Example 24

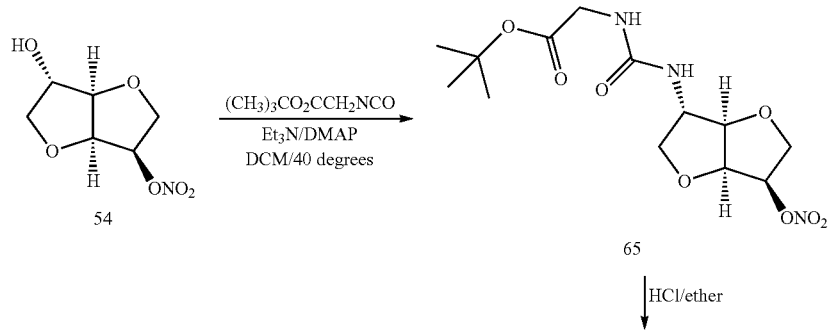

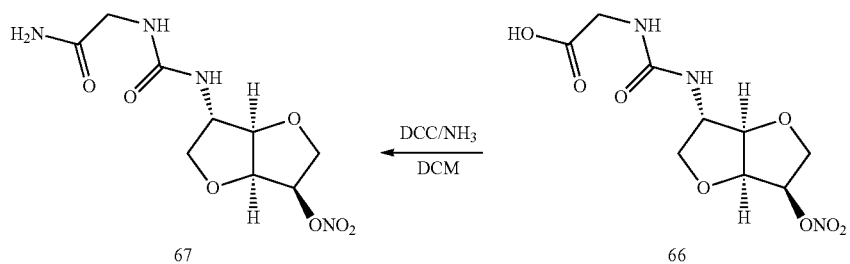

Treatment of isosorbide-5-mononitrate (54) with t-butyl-cyanoacetate in acetonitrile in the presence of N-methyl imidazole can yield the carbamate (65). Removal of the t-butyl group can be achieved with HCl in ether or with TFA to give the carboxylic acid (66). Amidation of the acid with ammonia in the presence of DCC can provide the carboxamide (67).

Synthesis Example 25

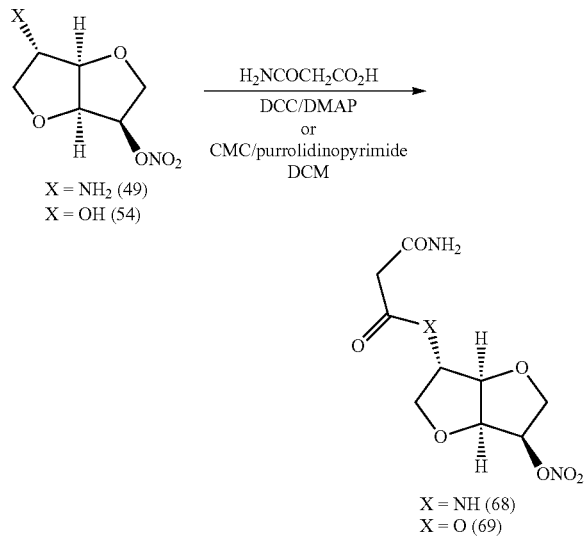

Treatment of 2-amino-isosorbide-5-mononitrate (49) or isosorbide-5-mononitrate (54) with malonic acid monoamide in DCM in the presence of DCC/DMAP or CMC/pyrrolidinopyrimidine can produce the malonamide (68) or the malono-ester-amido (69), respectively.

Synthesis Example 26

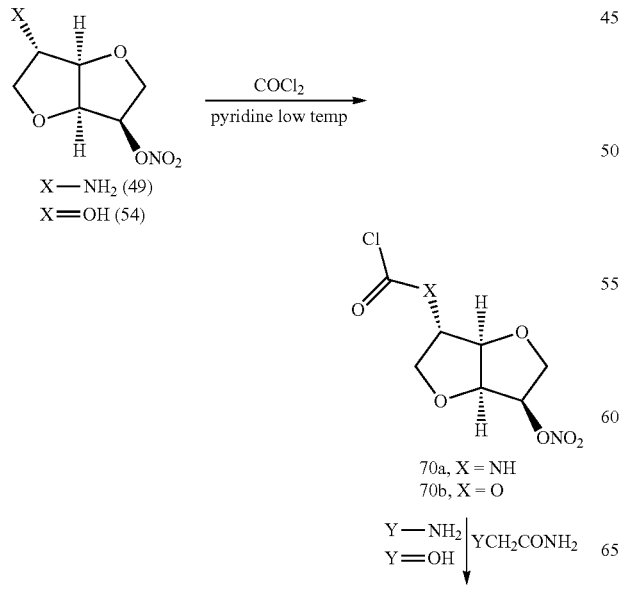

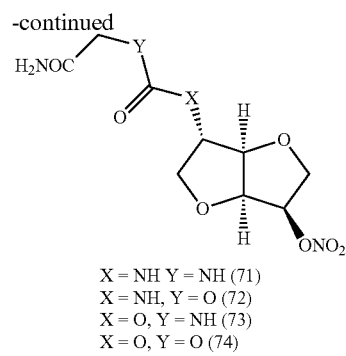

X = NH Y = NH (71)
X = NH, Y = O (72)
X = O, Y = NH (73)
X = O, Y = O (74)

Treatment of 2-amino-isosorbide-5-mononitrate (49) with phosgene and pyridine at about 0° C. can produce the carbamoyl chloride (70a, X=NH). Reaction of this carbamoyl chloride with glycinamide at low temperatures in the presence of DMAP in DCM can afford the ureido carboxamide (71). Alternatively, the carbamoyl chloride (70a, X=NH) can be treated with glycolamide in the presence of DMAP in DCM and to afford the carbonate with the terminal carboxamide group (72). If isosorbide-5-mononitrate (54) is used as the starting material for this sequence, the phosgene reaction can produce the carbonyl chloride at low temperature (70b, X=O) and if this intermediate is treated with glycinamide or glycolamide under the conditions previously described, the carbamate (73) or the carbonate (74), respectively, can be prepared.

Synthesis Example 27

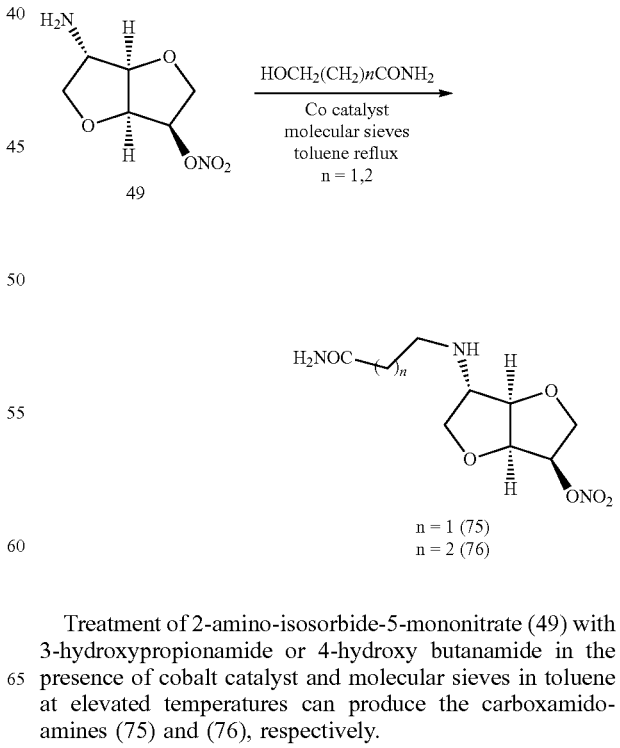

n = 1 (75)
n = 2 (76)

Treatment of 2-amino-isosorbide-5-mononitrate (49) with 3-hydroxypropionamide or 4-hydroxy butanamide in the presence of cobalt catalyst and molecular sieves in toluene at elevated temperatures can produce the carboxamidoamines (75) and (76), respectively.

Synthesis Example 28

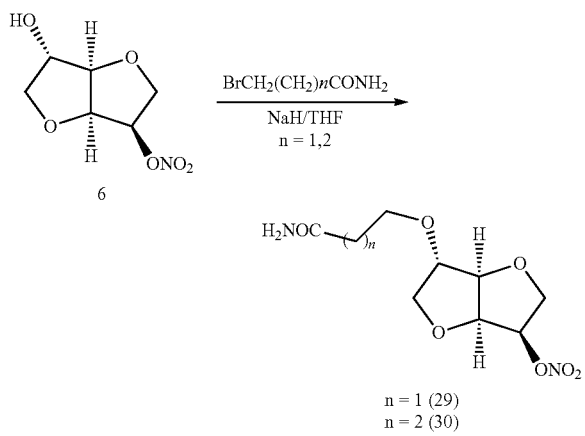

Treatment of isosorbide-5-mononitrate (6) with sodium hydride in THF or lithium diisopropylamide in THF and subsequent alkylation of the alkoxide with 3-bromoprionamide or 4-bromobutanamide can yield the carboxamido-ethers (77) and (78), respectively.

Synthesis Example 29

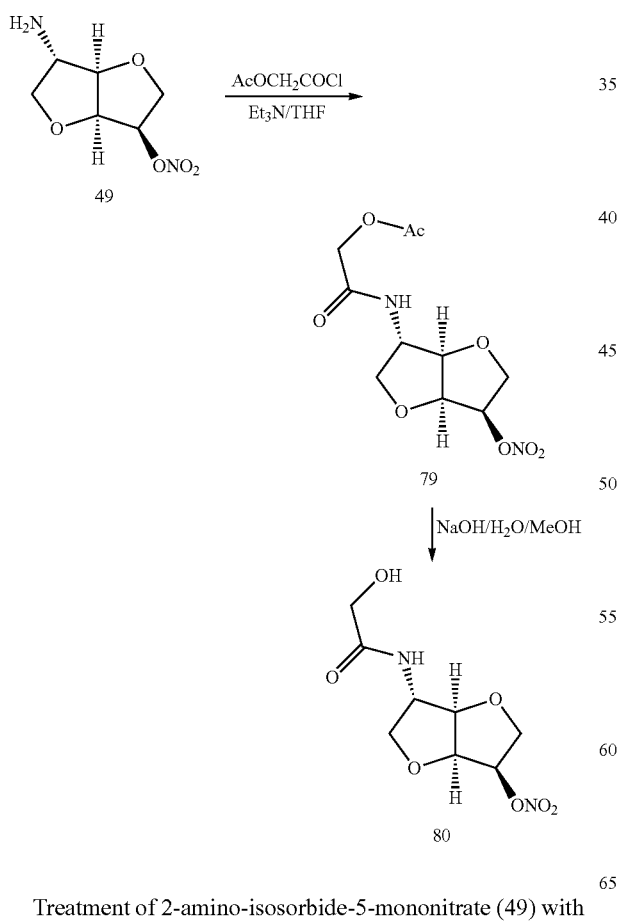

Treatment of 2-amino-isosorbide-5-mononitrate (49) with acetoxyacetyl chloride in the presence of triethylamine in THF can produce the amide adduct (79). Hydrolysis of the acetate with sodium hydroxide solution can produce the hydroxyl amide (80).

Synthesis Example 30

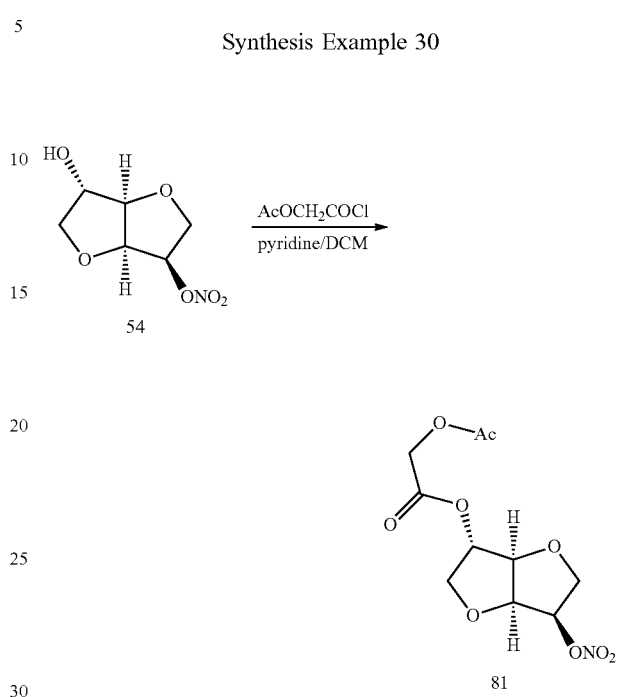

Treatment of isosorbide-5-mononitrate (54) with acetoxyacetyl chloride in the presence of triethylamine in THF can produce the ester adduct (81). Hydrolysis of the acetate with dibutyl tin oxide will produce the glycolic acid adduct (82).

Synthesis Example 31

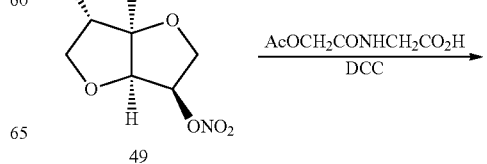

Synthesis Example 32

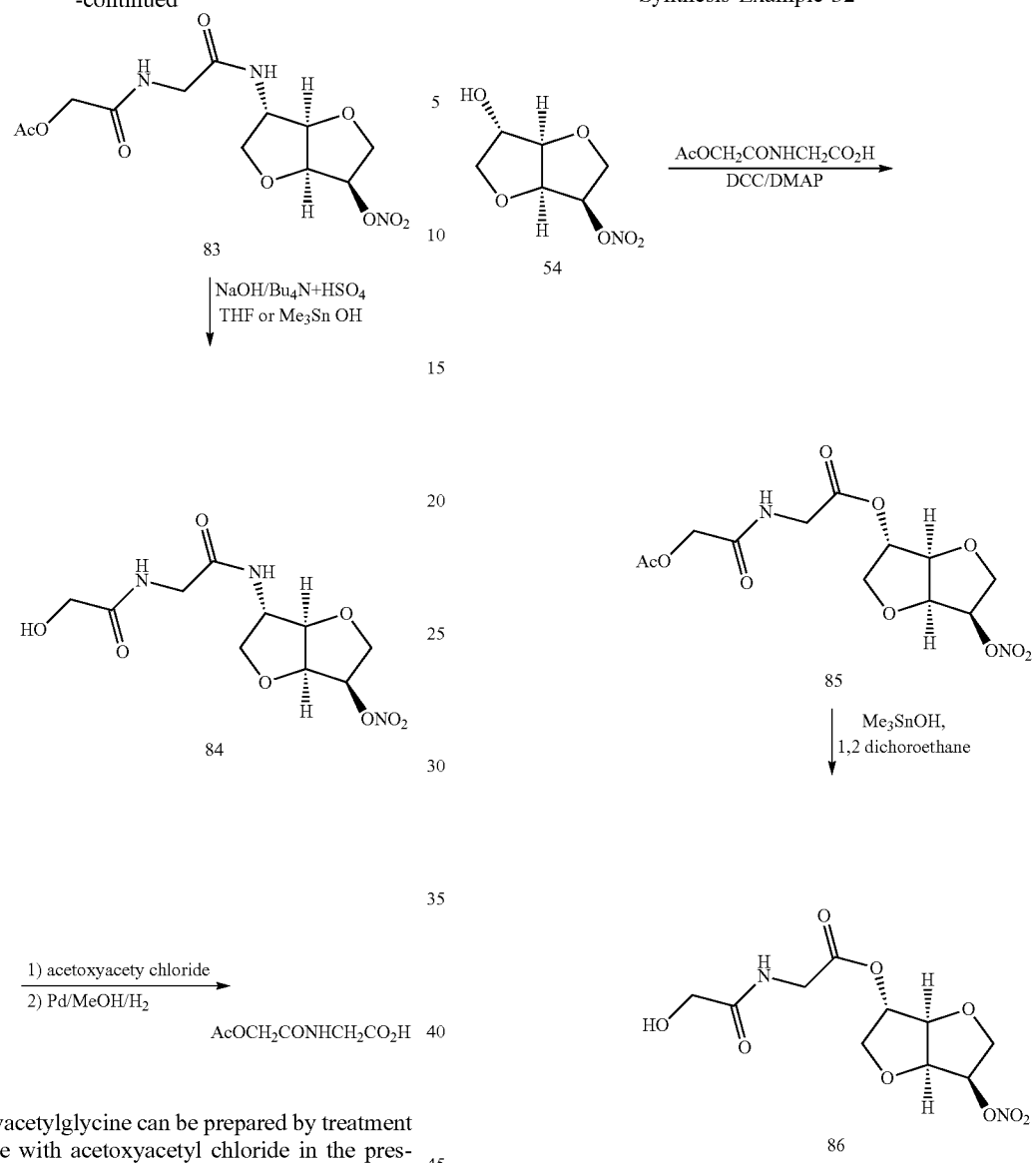

The N-acetoxyacetylglycine can be prepared by treatment of benzyl glycine with acetoxyacetyl chloride in the presence of triethylamine, followed by hydrogenolysis of the benzyl ester in the presence of palladium catalyst. Treatment of 2-amino-isosorbide-5-mononitrate (49) with acetoxy acetyl glycine in DCM in the presence of DCC can produce the acetylated amide adduct (83). Removal of the acetate (84) can be accomplished by reaction with KOH in methanol solution or with trimethyl tin hydroxide.

Treatment of isosorbide-5-mononitrate (6) with acetoxy acetyl glycine in DCM in the presence of DCC/DMP can produce the acetylated ester adduct (85). Removal of the acetate (86) can be accomplished by reaction with trimethyl tin hydroxide.

Synthesis Example 33

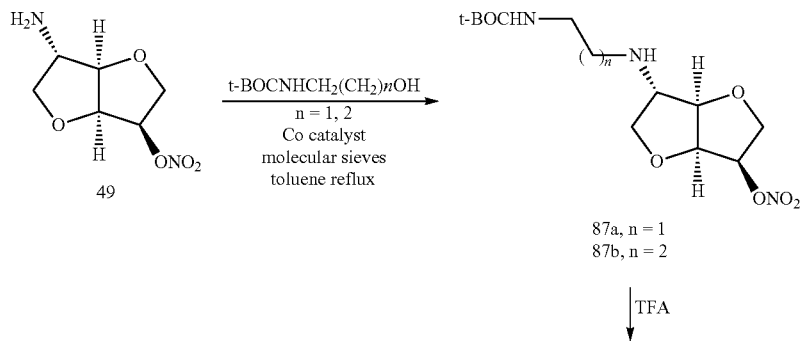

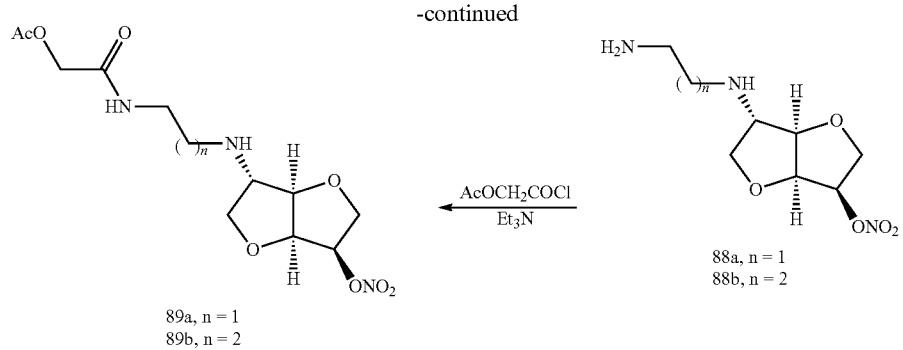

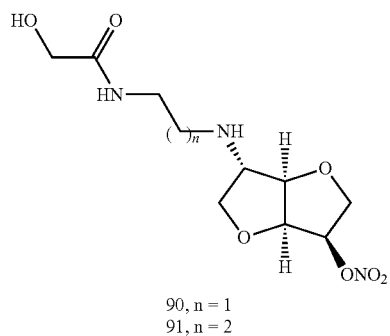

Treatment of 2-amino-isosorbide-5-mononitrate (49) with N-t-BOC-aminoethanol or N-t-BOC-3-aminopropanol in the presence of cobalt catalyst and molecular sieves in toluene at elevated temperatures can provide the protected amino compounds (87). Removal of the protecting group can be accomplished using TFA, which can give the unprotected primary amines (88). Reaction of the amines (88) with acetoxyacetyl chloride in the presence of trimethylamine can provide the amides (89), and subsequent treatment with KOH in methanol can afford the hydroxyacetamides (90 and 91).

Synthesis Example 34

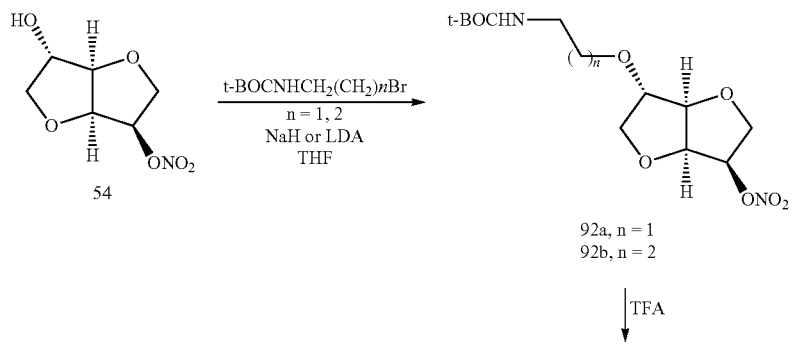

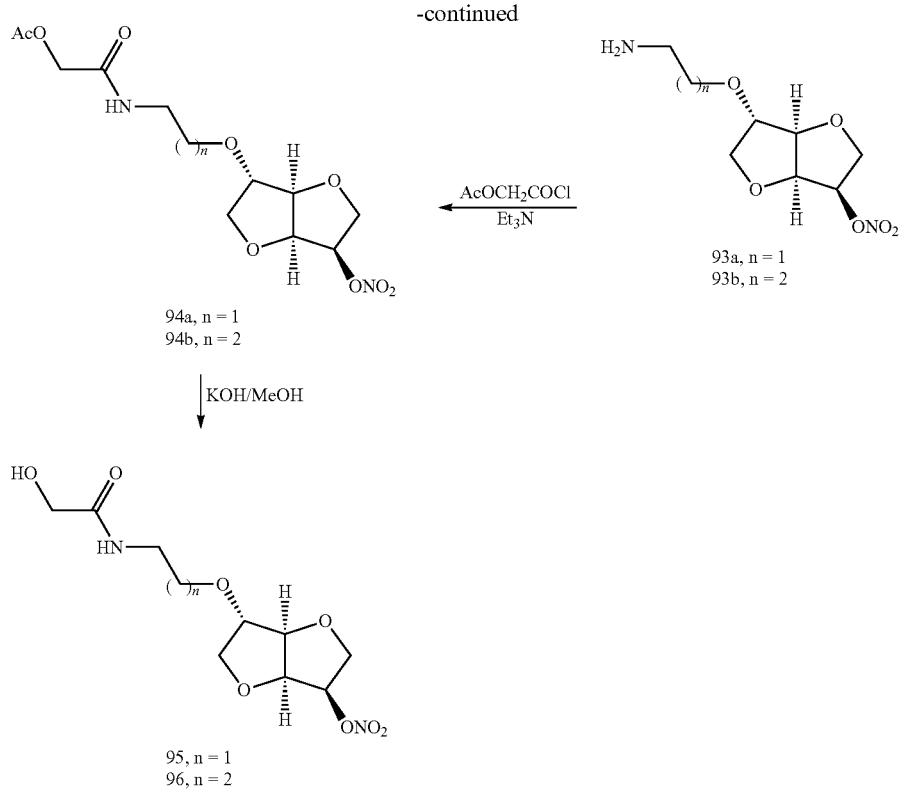

Deprotonation of isosorbide-5-mononitrate (54) with sodium hydride or LDA in THF followed by the addition of N-t-BOC-aminoethyl bromide or N-t-BOC-3-aminopropyl bromide can give the protected ethers (92). Deprotection of the amino groups using TFA can give the primary amines (93), which upon treatment with acteoxyacetyl chloride can give the amides (94). Hydrolysis of the acetate using KOH in MeOH can afford the hydroxacetamides (95 and 96).

Compound Examples

Tables 1-6 show the structures of compounds of the present invention that can be synthesized as described above.

TABLE 1

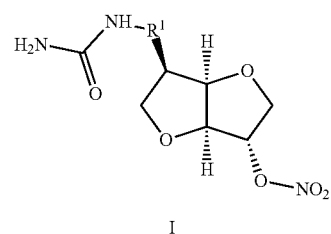

I

| Ex. # | $R^1$ |
|---|---|
| CR-0101 | Absent |
| CR-0102 | $(CH_2)_2O$ |

TABLE 1-continued

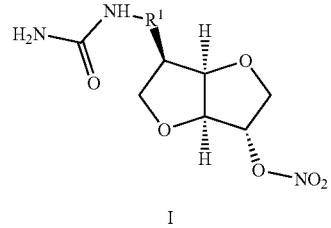

I

| Ex. # | $R^1$ |
|---|---|
| CR-0103 | $(CH_2)_2NH$ |
| CR-0104 | $(CH_2)_3O$ |
| CR-0105 | $(CH_2)_3NH$ |
| CR-0106 | $CH_2C(=O)O$ |
| CR-0107 | $CH_2C(=O)NH$ |

TABLE 2

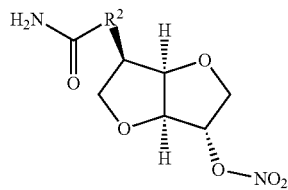

II

| Ex. # | $R^2$ |
|---|---|
| CR-0201 | $(CH_2)_2O$ |
| CR-0202 | $(CH_2)_2NH$ |

TABLE 2-continued

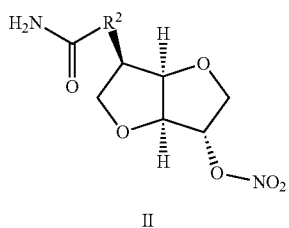

II

| Ex. # | R² |
|---|---|
| CR-0203 | (CH₂)₃O |
| CR-0204 | (CH₂)₃NH |
| CR-0205 | CH₂C(=O)O |
| CR-0206 | CH₂C(=O)NH |
| CR-0207 | CH₂OC(=O)O |
| CR-0208 | CH₂OC(=O)NH |
| CR-0209 | CH₂NHC(=O)O |
| CR-0210 | CH₂NHC(=O)NH |

TABLE 3

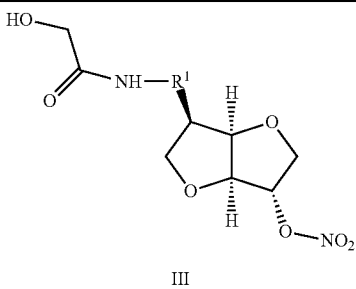

III

| Ex. # | R¹ |
|---|---|
| CR-0301 | Absent |
| CR-0302 | (CH₂)₂O |
| CR-0303 | (CH₂)₂NH |
| CR-0304 | (CH₂)₃O |
| CR-0305 | (CH₂)₃NH |
| CR-0306 | CH₂C(=O)O |
| CR-0307 | CH₂C(=O)NH |

TABLE 4

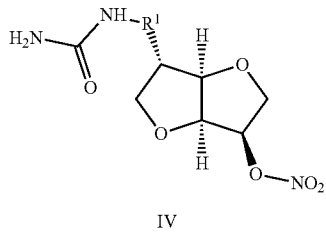

IV

| Ex. # | R¹ |
|---|---|
| CR-0401 | Absent |
| CR-0402 | (CH₂)₂O |
| CR-0403 | (CH₂)₂NH |
| CR-0404 | (CH₂)₃O |
| CR-0405 | (CH₂)₃NH |
| CR-0406 | CH₂C(=O)O |
| CR-0407 | CH₂C(=O)NH |

TABLE 5

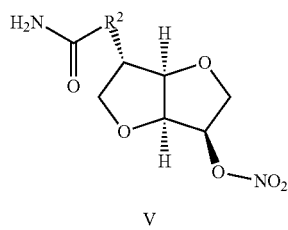

V

| Ex. # | R² |
|---|---|
| CR-0501 | (CH₂)₂O |
| CR-0502 | (CH₂)₂NH |
| CR-0503 | (CH₂)₃O |
| CR-0504 | (CH₂)₃NH |
| CR-0505 | CH₂C(=O)O |
| CR-0506 | CH₂C(=O)NH |
| CR-0507 | CH₂OC(=O)O |
| CR-0508 | CH₂OC(=O)NH |
| CR-0509 | CH₂NHC(=O)O |
| CR-0510 | CH₂NHC(=O)NH |

TABLE 6

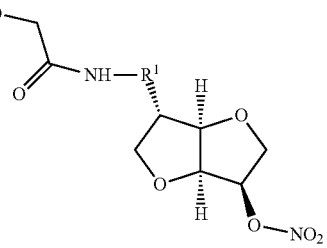

VI

| Ex. # | R¹ |
|---|---|
| CR-0601 | Absent |
| CR-0602 | (CH₂)₂O |
| CR-0603 | (CH₂)₂NH |
| CR-0604 | (CH₂)₃O |
| CR-0605 | (CH₂)₃NH |
| CR-0606 | CH₂C(=O)O |
| CR-0607 | CH₂C(=O)NH |

Synthesis of CR-0305

The synthesis began with a TBDPS-protected side-chain, Intermediate 4. A total of 1.01 g of Intermediate 4 was prepared as an oil in 44% overall yield.

Side Chain Synthesis

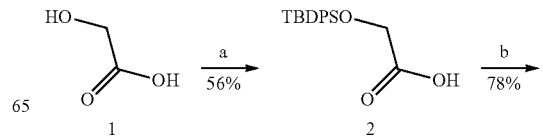

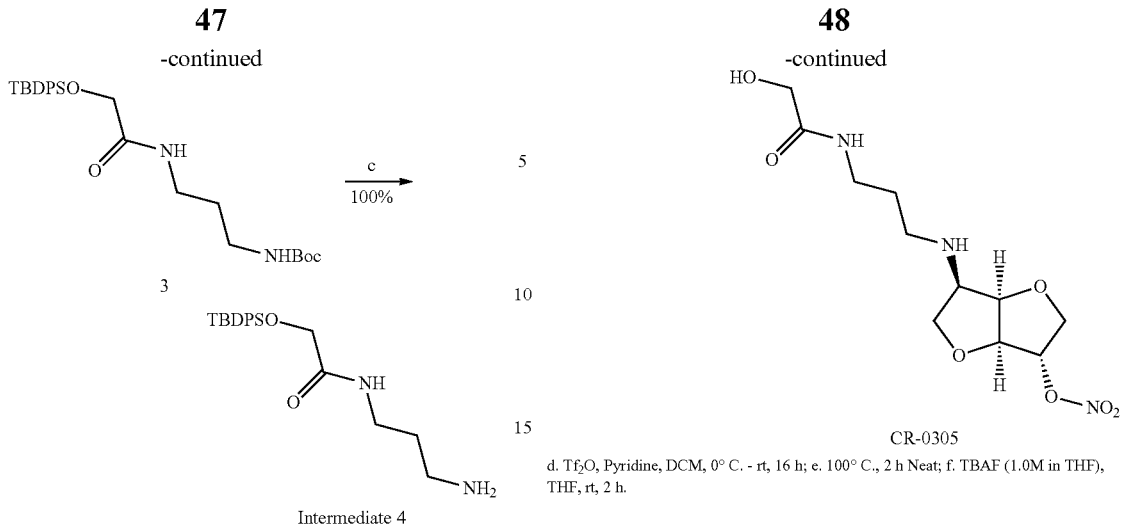

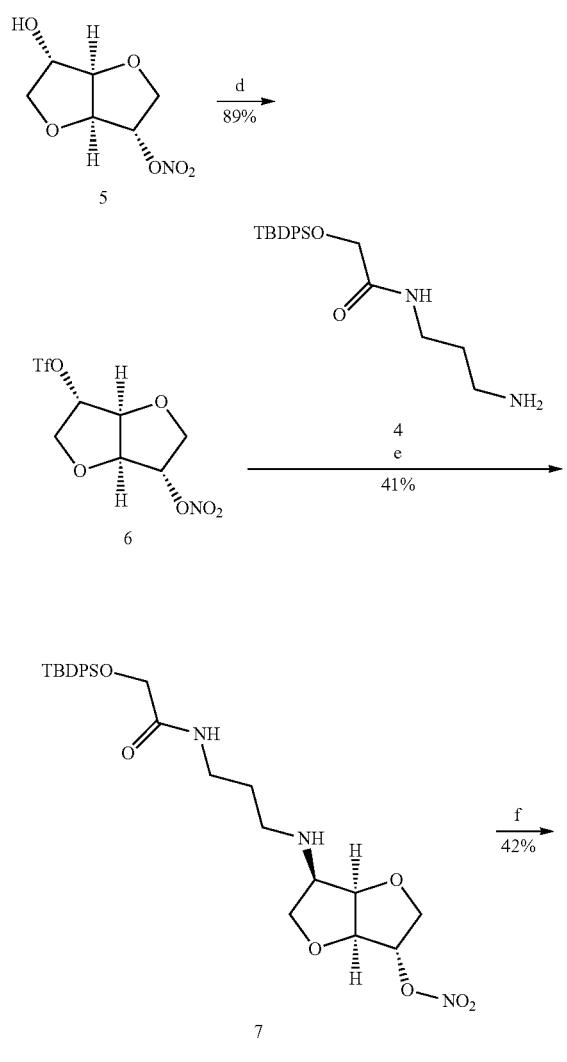

a. 1) DMAP/TEA, TMSCl, THF, 0° C. - rt 2 h then 2) TEA, TBDPSCl, rt 16 h; b. TEA, N-Boc-1,3-propanediamine, EDC, HOBt, rt, 24 h; c. TFA, DCM, 0° C. - rt, 2 h.

Intermediate 4 was prepared as shown above.

Final CR-0305 Synthesis d. Tf$_2$O, Pyridine, DCM, 0° C. - rt, 16 h; e. 100° C., 2 h Neat; f. TBAF (1.0M in THF), THF, rt, 2 h.

1,4:3,6-Dianhydro-L-Iditol Mononitrate (5): This compound was prepared in 2 steps by inverting stereochemistry at the hydroxyl position of Isosorbide 2-mononitrate, using a Mitsunobu coupling/De-benzoylation protocol as described. (Rajput, Gaikwad et al. 2014) The resulting 1,4:3,6-Dianhydro-L-Iditol Mononitrate was obtained in overall 71% yield as a waxy crystalline solid; Rf=0.48 (60% EA/Hept).

1,4:3,6-Dianhydro-L-Iditol Triflate Mononitrate (6): 160 mg of (5) was dissolved in dichloromethane (10 mL) followed by pyridine (75 mg, 0.95 mmol). The solution was chilled to 0° C. under nitrogen and trifluoromethanesulfonic anhydride added dropwise with stirring, then warmed to room temperature and stirred overnight. The solution was filtered through celite and rinsed with cold dichloromethane, evaporated and then purified by column chromatography (12 g ISCO) eluting with EA/Heptane (0-50%) to obtain as product a clear oil containing 236 mg, 87% 1,4:3,6-Dianhydro-L-Iditol Triflate Mononitrate (Compound 6); Rf=0.80 (40% EA/Hept).

(3S,3aS,6R,6aR)-6-((3-(2-((tert-butyldiphenylsilyl)oxy) acetamido)propyl)amino) hexahydrofuro[3,2-b]furan-3-yl nitrate (7): 1,4:3,6-Dianhydro-L-Iditol Triflate Mononitrate (6) (84 mg, 0.26 mmol) was combined with Intermediate 4 (193 mg, 0.52 mmol) as a solution in 1 mL of Dioxane. The mixture was stirred at 100° C. under a stream of nitrogen allowing solvent to evaporate. After 2 hours the solvent has completely evaporated and the mixture has turned from clear yellow to a red-orange paste. The reaction mixture was cooled to room temperature and TLC (60% ethyl acetate/heptane) indicates complete reaction. Crude product was purified by column chromatography (12 g ISCO) eluting with MeOH/DCM (5-20%) affording (7) as an oil (90 mg, 64%); Rf=0.60 (15% MeOH/EA).

(3S,3aS,6R,6aR)-6-((3-(2-hydroxyacetamido)propyl) amino)hexahydrofuro[3,2-b]furan-3-yl nitrate (CR-0305): Intermediate (7) (80 mg, 0.15 mmol) was dissolved in anhydrous THF (5 mL) under nitrogen and a TBAF solution (1.0M in THF, 190 μL, 0.19 mmol) added dropwise at room temperature. After 2 hours TLC (10% MeOH/DCM w/CAM stain) indicates complete reaction. Solvent was evaporated and the crude product purified by column chromatography (4 g ISCO) eluting with MeOH/DCM (1-20%) affording CR-0305 as an oil (22 mg, 49%); Rf=0.40 (10% MeOH/DCM).

Synthesis of CR-0202

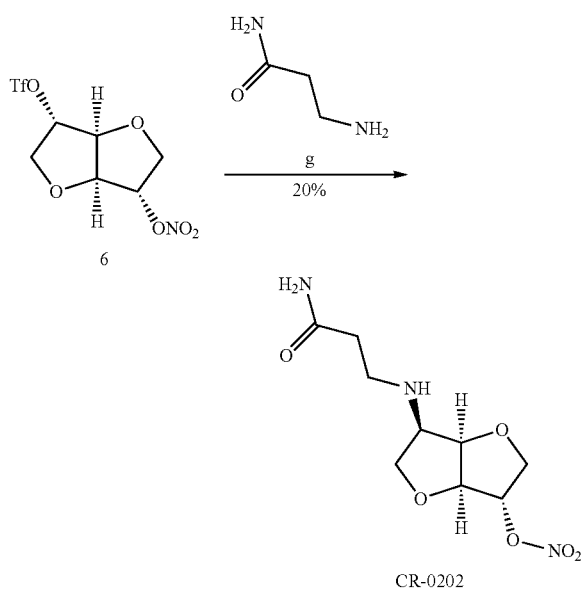

g. 80° C., 18 h, Neat.

(3S,3aS,6R,6aR)-6-((3-amino-3-oxopropyl)amino)hexahydrofuro[3,2-b]furan-3-yl nitrate (CR-0202): Compound (6) (100 mg, 0.31 mmol) was combined with 3-aminopropanamide (33 mg, 0.37 mmol) as a solution in 1 mL of Dioxane. The mixture was stirred at 80° C. under a stream of nitrogen allowing solvent to evaporate. After 2 hours the solvent has completely evaporated and the mixture has turned from clear yellow to a red-orange paste. The reaction mixture was cooled to room temperature and TLC (10% MeOH/DCM) indicates complete reaction. Crude product was purified by column chromatography (4 g ISCO) eluting with MeOH/DCM (1-20%) affording CR-0202 as a foamy solid (19 mg, 23%); Rf=0.20 (10% MeOH/DCM).

Toxicity

CR-0305 and CR-0202 were tested against isosorbide-2-nitrate, isosorbide dinitrate and GRL-0617 for evidence of mitochondrial toxicity and changes in total cellular ATP in response to treatment, using concentrations relevant to the known human serum concentrations of isosorbide-2-nitrate (1-2 µM.)

MitoCheck Complex I-V activity assays were conducted in an Agilent Seahorse XFe96 analyzer to determine the effects of compounds on the mitochondrial electron transport chain and ATP synthase in isolated mitochondria. Compounds were screened in a dose dependent manner using 10-point ½ log dilutions in quadruplicate along with a vehicle positive control for each of the five complexes.

Complex I activity was determined using an assay that measures the rotenone-sensitive rate of NADH oxidation by complex I in isolated bovine heart mitochondria. To prevent oxidation of ubiquinol by complex III, KCN (1 mM) was present to inhibit the downstream electron transport chain. The positive control for this assay is rotenone at a starting concentration of 10 µM.

Complex II activity was determined using an assay that measures the succinate dependent rate of DCPIP reduction in isolated bovine heart mitochondria. To prevent oxidation of ubiquinone by complex III, and reverse electron transfer from complex II to complex I, antimycin A (10 µM), KCN (1 mM), and rotenone (1 µM) were present for all experiments. The positive control for this assay is 2-thenoyltrifluoroacetone (TTFA) at a starting concentration of 10 mM.

Complex III activity was determined using an assay measures the rate of cytochrome c reduction by the passage of electrons from complex II to complex III via ubiquinone in isolated bovine heart mitochondria. To prevent oxidation of cytochrome c by complex IV, KCN (1 mM) was present for all experiments. The positive control for this assay is antimycin A at a starting concentration of 10 µM.

Complex IV activity was determined using an assay that measures the rate of cytochromec oxidation by complex IV in isolated bovine heart mitochondria. The positive control for this assay is KCN at a starting concentration of 10 mM.

Complex V activity was determined using an assay that measures the rate of NADH reduction resulting from a series of coupled reactions linked to the hydrolysis of ATP by complex V in isolated bovine heart mitochondria. Rotenone (1 µM) was present to prevent NADH oxidation by complex I. Since no inhibition was reported, counter screens to test for inhibition of non-specific ATPases were not performed. The positive control for this assay is oligomycin at a starting concentration of 10 µM.

A mitochondrial stress test was also conducted to determine the effects of the experimental compounds on cellular mitochondria. Assays were conducted using HMEC-1 human dermal endothelial cells optimized for use with the Agilent Seahorse XFe96 analyzer. HMEC-1 cells were obtained from ATCC and cultured in accordance with the supplier's guidelines: complete cell culture media consisted of MCD 131 supplemented with 10 ng/ml EGF 1 µg/ml hydrocortisone, 10 mM glutamine, 10% FBS, and 1% penicillin/streptomycin. To determine optimal cell seeding densities, cells were seeded in Agilent XF96 cell culture microplates at 80,000 cells/well at the highest concentration. An 8-point, two-fold dilution of cells occurred every row thereafter (range=80,000-600 cells/well), and cells cultured overnight under standard conditions. Criteria for optimization included a baseline oxygen consumption rate (OCR) between 75 and 150 pmol/min and a concentration of FCCP that will maximally increase OCR without causing inhibition. Based on these titrations optimal cell seeding density and FCCP concentration was found to be 25,000 cells/well and 2 µM FCCP. In the stress test, HMEC-1 cells seeded on XFe96 Cell Culture Microplates at 25,000 live cells/well in complete media and cultured for 18 hours at 37° C./5% $CO_2$ were used. Cell viability was assessed using trypan blue exclusion. The following morning, complete media was exchanged for XF Assay medium (XF DMEM supplemented with 10 mM glucose, 1 mM pyruvate and 2 mM glutamine) using the media exchange program for the Agilent Bravo automated liquid handler. Following media exchange, the cell plate was incubated at 37° C. (non-$CO_2$) for 1 hour and imaged with a Cytation 5 imaging multimode plate reader (BioTek instruments) and analyzed using Prism 9.0 (GraphPad Software.) The stress test profile cycled through 18 minute exposures to oligomycin 1 µg/ml, FCCP 2 µM and antimycin A 10 µM/rotenone 1 µM. At the completion of the mitochondrial stress test, cells were imaged and Hoechst positive nuclei were quantified using the Seahorse Cell Analysis software. All data were analyzed using Wave Analysis software (version 2.6.1.53) and Prism 9.0 (GraphPad software). Final DMSO concentration for all conditions was 0.1%.

The Cell TiterGlo ATP Luminescent Cell Viability assay (Promega Cat. #G7571) was run to measure total cellular ATP in response to compound treatment. Assays were performed using HMEC-1 human dermal endothelial cells. Compounds were screened using 8-point ½ log dilutions in duplicate in the presence of vehicle. HMEC-1 cells were studied in culture in triplicate exposures to CR-0305, CR-0202, isosorbide-2-nitrate and GRL-0617 at 10 µM, 3 µM, 1 µM, 300 nM, 100 nM, 30 nM, 10 nM and 3 nM for 18 hours, and cellular ATP was measured using the CellTiter-Glo® Luminescent Cell Viability assay (Promega Cat. #G7571.) Controls were used with mock treatment of solvent and media alone, along with a positive control 10 mM doxorubicin.

Toxicity of CR-0305 was examined using MitoCheck Complex I-V activity assays in isolated mitochondria as well as a mitochondrial stress test in HMEC-1 conducted using an Agilent Seahorse XFe96 analyzer followed by measurement of the effect of drug on ATP synthesis in HMEC-1. No significant toxicity was identified at 10-100 µM concentrations.

Biology

The novel compounds were subjected to virtual screening against SARS-CoV-2 proteins, through in silico modelling against nine SARS-CoV-2 targets using Maestro Schrödinger Suite software with Glide docking. (Friesner, Murphy et al. 2006) Criteria for selection of virtual hits included docking scores and intermolecular interactions within the target's key binding pocket's amino acid residues. (Greenwood, Calkins et al. 2010) Compound characteristics and predicted physicochemical ADME/Tox properties were also calculated using Qikprop, Schrödinger Release 2020-2. SARS-CoV-2 targets included: Main protease, 3CLpro (Nsp5), Spike Glycoprotein, Angiotensin Converting Enzyme 2, ACE2 (human), RNA-Dependent RNA Polymerase, RdRp (Nsp12), Endoribonuclease (Nsp15), Guanine-N7 methyltransferase (Nsp14), Papain-Like proteinase, PLpro (Nsp3), ADP-ribose phosphatase of Nsp3, and Bromodomain 2, BRD2 (human.) The reported structure for each of the 9 targets were individually modified using Maestro Protein Preparation Wizard selecting default values. Water molecules at 5 Å from heteroatoms were eliminated. Protonation state of side chains were modified with Epik between pH 5-9. (Shelley, Cholleti et al. 2007) Positions of hydrogen bonds and torsion angles were refined prior to initiation, including the addition of missing side chains. Disulfide bonds were allowed to exist. Water orientations were sampled at pH 7.

These protein targets were matched against 59 compound structures including 48 novel compound structures of the present invention (see U.S. Pat. Nos. 10,501,471 and 10,913,748)(nomenclature defined below), as well as a drug show to have efficacy in treatment of COVID-19, Remdesivir (Beigel, Tomashek et al. 2020), its main plasma metabolite GS-441524 and GS-441524 triphosphate, the antiviral Ribavarin, the PL$^{pro}$ inhibitor GRL-0617 (Shin, Mukherjee et al. 2020), isosorbide dinitrate, 1,4:3,6-dianhydro-D-glucitol, 1,4:3,6-dianhydro-L-iditol, (3S,3aS,6R,6aR)-6-aminohexahydrofuro[3,2-b]furan-3-yl nitrate, isosorbide 5-nitrate, and isosorbide 2-nitrate.

Nomenclature for Current Compounds. The presently tested compounds include those of formula I, II, III, IV, V and/or VI, wherein the compounds are numbered as follows:
a. when $R^1$ is
  1. absent
  2. $(CH_2)_2O$
  3. $(CH_2)_2NH$
  4. $(CH_2)_3O$
  5. $(CH_2)_3NH$
  6. $CH_2C(=O)O$
  7. $CH_2C(=O)NH$.
b. when $R^2$ is
  1. $(CH_2)_2O$
  2. $(CH_2)_2NH$
  3. $(CH_2)_3O$
  4. $(CH_2)_3NH$
  5. $CH_2C(=O)O$
  6. $CH_2C(=O)NH$
  7. $CH_2OC(=O)O$
  8. $CH_2OC(=O)NH$
  9. $CH_2NHC(=O)O$
  10. $CH_2NHC(=O)NH$ CR-XXYY number scheme is based on XX=formula number and YY=number $R^1$ or $R^2$ group associated with the formula number. Therefore, compound III-5 was created from formula III and features the fifth $R^1$ group and was named CR-0305.

Control compounds were included in the Glide docking jobs for each of the SARS-CoV-2 targets, as follows:
  Main protease (3CLpro): Lopinavir, Boceprevir and α-ketoamide,
  Spike glycoprotein and ACE2 (human): Bimosiamose
  RdRp (Nsp12): Ribavirin
  Endoribonuclease (Nsp15) and Guanine-N7 methyltransferase (Nsp14): Ribavirin
  PLpro (Nsp3): GSK2251052 hydrochloride
  ADP-ribose phosphatase of Nsp3: ADP-ribose
  BRD2 (human): JQ1 and PFI1

Focusing on high-performance ligand-receptor docking, rigid-dock (Glide, Schrödinger Suite) was chosen as the screening model of compounds for affinity towards 9 SARS-CoV-2 protein targets. No constraints were considered in these docking screens (less-biased model). Based on the recent reported structures for these targets, crucial intermolecular hydrogen bonds within the amino acid residues of the binding pocket and compound, as well as docking scores were main drivers in rank-ordering compounds in this in silico screening program. Upon successful completion of the Glide job, docking experiments poses for each compound were assessed by Glide score, a prediction of ligand affinity. As it simulates a binding free energy, more negative values represented tighter binders. Secondly, they were assessed by Emodel score which is a measure of pose strength and validity.

Some of the compounds were identified as having strong metrics that outperformed the control compounds and existing approved-drugs against a few of the proteins such as PLpro (Nsp3) (FIGS. 1A-D) and ADP-ribose phosphatase of Nsp3. (FIGS. 2A-D) Evidently the novel compounds act on Nsp3 at these two locations with specific avidity, suggesting that they have an important function on Nsp3, presumably inhibiting virus replication while stopping PLpro antagonism of the innate immune response. (Baez-Santos, St John et al. 2015)

For the remaining targets, top hits either scored similar to control compounds (such as 3CL$^{pro}$, Spike glycoprotein, RdRp, Nsp15 and BRD2) or slightly lower than the control compounds (such as ACE2 and Guanine-N7 Methyltransferase of Nsp3). For PL$^{pro}$, about 10 compounds which scored higher and/or equal to control compounds (GSK2251052 hydrochloride, Remdesivir, Ribavirin, RTP) were identified as strong hits: such as CR-0305, CR-0607, CR-0510, and CR-0201. They were further evaluated for their binding interactions within the catalytic pocket. For ADP-ribose phosphatase, about 6 compounds scored equally compared to the control compound (ADP-ribose, enzyme substrate) such as CR-0504, CR-0502, CR-0503, CR-0506, CR-0203, and CR-0510. Based on the generated PLpro docking model, CR-0305, CR-0607, and CR-0510 compounds were bound in the active site of the enzyme similar to Ribavirin. (Wu, Liu et al. 2020) Key hydrogen bonds were predicted between Gly163, Asp164, Gly271, Tyr264 and compound. These interactions between top hits with the enzyme suggests the potent inhibitory effect of these compounds against $PL^{pro}$.

The present novel agents appear to bind with increased avidity to the PLpro and the ADP-ribose phosphatase domains of Nsp3 (Lei, Kusov et al. 2018) compared with other known antivirals while targeting delivery of NO to the SARS-CoV-2 virus in COVID-19. Evidently the novel compounds act on Nsp3 at these two locations with specific avidity, suggesting that they have an important function on Nsp3, presumably inhibiting virus replication while stopping PLpro antagonism of the innate immune response. CR-0305 was superior to GRL-0617, Remdesivir, GS-441524, Lopinavir, Boceprevir, and Ribavirin in binding PLpro. CR-0305 appears to have a higher affinity to SARS-CoV-2 than other antivirals as it sits firmly in the PLpro catalytic pocket and makes the most of critical interactions with the key catalytic pocket amino acids Gly163, Asp164, Gly271 and Tyr264. In all, there were ten compounds whose affinity as ligands to PLpro scored higher and/or equal to control compounds (GSK2251052 hydrochloride, Remdesivir, Ribavirin, RTP, GRL-0617) and several were identified as strong hits: such as CR-0305, CR-0607, CR-O519 and CR-0201. These hits were then ranked via Molecular Mechanics/Generalized Born Surface Area (MM/GBSA) calculations using the Schrödinger Suite Prime software package on top poses to predict binding free energies of hit compounds, provide better enrichment and to rank in order the docked pose of compounds. Scores summarized in Table A.

TABLE A

Compounds Binding to $PL^{pro}$

| | Prime MM/GBSA dG | Glide Score (kcal/mol) | Emodel Score |
|---|---|---|---|
| CR-0305 | −57.51 | −7.329 | −56.858 |
| CR-0607 | −44.38 | −6.882 | −56.269 |
| CR-0307 | −41.79 | −6.827 | −45.819 |
| CR-0510 | −42.09 | −6.449 | −54.627 |
| CR-0605 | −49.69 | −6.263 | −56.804 |
| RTP | −32.5 | −6.147 | −53.27 |
| CR-0201 | −33.2 | −6.064 | −51.058 |
| alpha-ketoamide | | −5.903 | −70.513 |
| Remdesivir | −36.84 | −5.871 | −61.628 |
| Ribavirin | −30.49 | −5.82 | −46.403 |
| CR-0103 | −43.88 | −5.83 | −55.421 |
| CR-0204 | −46.52 | −5.747 | −54.92 |
| CR-0101 | −33.09 | −5.619 | −46.491 |
| CR-0506 | −35.28 | −5.607 | −55.199 |
| CR-0508 | −41.17 | −5.594 | −53.101 |
| CR-0206 | −40.25 | −5.56 | −54.239 |
| CR-0301 | −34.17 | −5.487 | −48.697 |
| CR-0403 | −34.22 | −5.453 | −49.416 |
| CR-0107 | −37.63 | −5.374 | −52.948 |
| CR-0606 | −35.28 | −5.355 | −48.416 |
| CR-0302 | | −5.332 | −53.024 |
| CR-0601 | | −5.273 | −47.677 |
| CR-0210 | | −5.255 | −51.841 |
| CR-0401 | | −5.205 | −45.562 |

TABLE A-continued

Compounds Binding to $PL^{pro}$

| | Prime MM/GBSA dG | Glide Score (kcal/mol) | Emodel Score |
|---|---|---|---|
| CR-0303 | | −5.203 | −51.092 |
| CR-0504 | | −5.198 | −43.504 |
| CR-0203 | | −5.172 | −48.871 |
| GRL0617 | −26.3 | −5.152 | −43.591 |
| CR-0503 | | −5.15 | −47.168 |
| CR-0402 | | −5.127 | −44.861 |
| CR-0306 | | −5.107 | −53.021 |
| CR-0406 | | −5.091 | −44.582 |
| CR-0209 | | −5.069 | −51.846 |
| CR-0502 | | −5.047 | −46.083 |
| CR-0106 | | −5.004 | −50.705 |
| CR-0304 | | −4.993 | −48.802 |
| GS-441524 | −30.15 | −4.95 | −45.88 |
| CR-0205 | | −4.936 | −50.937 |
| CR-0208 | | −4.919 | −50.588 |
| CR-0102 | | −4.909 | −48.039 |
| CR-0202 | | −4.893 | −44.644 |
| CR-0501 | | −4.89 | −48.118 |
| 1,4:3,6-dianhydro-D-glucitol | | −4.879 | −29.831 |
| Lopinavir | | −4.822 | −48.575 |
| 1,4:3,6-dianhydro-L-iditol | | −4.812 | −30.411 |
| CR-0407 | | −4.809 | −51.083 |
| CR-0507 | | −4.751 | −49.661 |
| CR-0509 | | −4.614 | −44.742 |
| CR-0604 | | −4.558 | −49.034 |
| JQ1 | | −4.553 | −52.148 |
| (3S,3aS,6R,6aR)-6-aminohexahydrofuro[3,2-b]furan-3-yl nitrate | | −4.546 | −33.765 |
| CR-0505 | | −4.54 | −45.489 |
| CR-0207 | | −4.502 | −44.971 |
| Isosorbide 5-Nitrate | | −4.342 | −35.096 |
| GSK2251052hydrochloride | | −4.307 | −38.976 |
| Isosorbide 2-Nitrate | | −4.306 | −32.169 |
| CR-0105 | | −4.159 | −49.024 |
| Boceprevir | | −4.105 | −44.717 |
| Isosorbide dinitrate | −22.01 | −3.97 | −39.446 |
| CR-0104 | | −3.821 | −42.205 |
| CR-0405 | | −3.803 | −44.337 |
| CR-0404 | | −3.113 | −42.918 |
| CR-0602 | | −3.1 | −45.633 |
| CR-0603 | | −2.994 | −40.359 |

For ADP-ribose phosphatase, about 6 compounds scored equally compared to the control compound (ADP-ribose, enzyme substrate) such as CR-0504, CR-0502, CR-0503, CR-0506, CR-0201 and CR-0510. For the remaining targets, top hits either scored very similar to control compounds (such as $3CL^{pro}$, Spike glycoprotein, RdRp, Nsp15 and BRD2) or slightly lower than the control compounds (such as ACE2 and Guanine-N7 Methyltransferase of Nsp3). Lower Glide and Emodel scores were mostly due to the smaller size of some compounds compared to the controls. For instance, 3CLpro and Spike Receptor-Binding-Domain (RBD) binding sites are large, near surface and solvent exposed which require larger compounds to fit thoroughly in the pocket. Scores summarized in Table B.

TABLE B

Compounds Binding to ADP ribose phosphtatase

| | Glide Score (kcal/mol) | Emodel Score |
|---|---|---|
| ADP ribose | −8.748 | −91.45 |
| CR-0504 | −8.208 | −75.864 |
| CR-0502 | −8.18 | −69.377 |
| CR-0503 | −8.163 | −74.852 |
| CR-0506 | −8.114 | −73.33 |

TABLE B-continued

Compounds Binding to ADP ribose phosphtatase

| | Glide Score (kcal/mol) | Emodel Score |
|---|---|---|
| CR-0203 | −8.051 | −70.611 |
| CR-0510 | −7.887 | −74.522 |
| CR-0501 | −7.734 | −73.684 |
| CR-0505 | −7.666 | −66.792 |
| CR-0402 | −7.66 | −66.431 |
| CR-0204 | −7.507 | −63.506 |
| CR-0406 | −7.455 | −66.126 |
| CR-0202 | −7.388 | −52.914 |
| CR-0210 | −7.363 | −60.259 |
| CR-0407 | −7.313 | −68.49 |
| 1,4:3,6-dianhydro-L-iditol | −7.277 | −47.421 |
| CR-0604 | −7.249 | −65.716 |
| CR-0403 | −7.144 | −62.223 |
| CR-0307 | −7.121 | −60.537 |
| CR-0509 | −7.116 | −64.66 |
| CR-0606 | −7.028 | −63.016 |
| RTP | −7.027 | −69.012 |
| CR-0103 | −7.024 | −60.409 |
| CR-0507 | −7.021 | −62.729 |
| CR-0207 | −6.934 | −60.746 |
| CR-0205 | −6.915 | −60.421 |
| CR-0607 | −6.909 | −62.708 |
| CR-0201 | −6.897 | −66.57 |
| CR-0208 | −6.77 | −59.562 |
| (3S,3aS,6R,6aR)-6-aminohexahydrofuro[3,2-b]furan-3-yl nitrate | −6.769 | −49.654 |
| CR-0101 | −6.761 | −54.485 |
| CR-0102 | −6.743 | −60.886 |
| CR-0107 | −6.685 | −62.969 |
| CR-0106 | −6.666 | −62.298 |
| 1,4:3,6-dianhydro-D-glucitol | −6.666 | −42.515 |
| CR-0104 | −6.658 | −67.611 |
| CR-0209 | −6.524 | −59.006 |
| CR-0508 | −6.419 | −63.193 |
| CR-0306 | −6.379 | −60.08 |
| CR-0304 | −6.378 | −59.214 |
| CR-0206 | −6.374 | −59.975 |
| CR-0301 | −6.313 | −52.48 |
| CR-0305 | −6.086 | −58.266 |
| CR-0605 | −6.084 | −62.388 |
| CR-0601 | −6.03 | −53.132 |
| CR-0401 | −5.972 | −50.512 |
| Isosorbide2-Nitrate | −5.802 | −48.525 |
| CR-0602 | −5.775 | −64.34 |
| Isosorbide5-Nitrate | −5.577 | −45.192 |
| Furan | −5.497 | −37.655 |
| CR-0405 | −5.376 | −63.177 |
| CR-0303 | −5.362 | −56.969 |
| CR-0302 | −5.35 | −58.337 |
| CR-0105 | −5.327 | −56.197 |
| CR-0404 | −5.198 | −59.909 |
| CR-0603 | −5.032 | −63.41 |
| CR-0105 | −4.771 | −49.266 |
| Remdesivir | −4.294 | −32.681 |
| GS-441524 | −4.019 | −35.02 |

Using the crystal structure of SARS-CoV-2 PL$^{pro}$ (6WUU PDB ID) to study MD (Molecular Dynamics) we performed a 20+ ns simulation to confirm the stability of the small molecules and protein binding pocket contacts and water networks. (Hollingsworth and Dror 2018) Based on the MD simulation results for CR-0305 compound, additional contacts were observed between compound/protein around residues 110-113 compared to the reference.

Figure 3A:
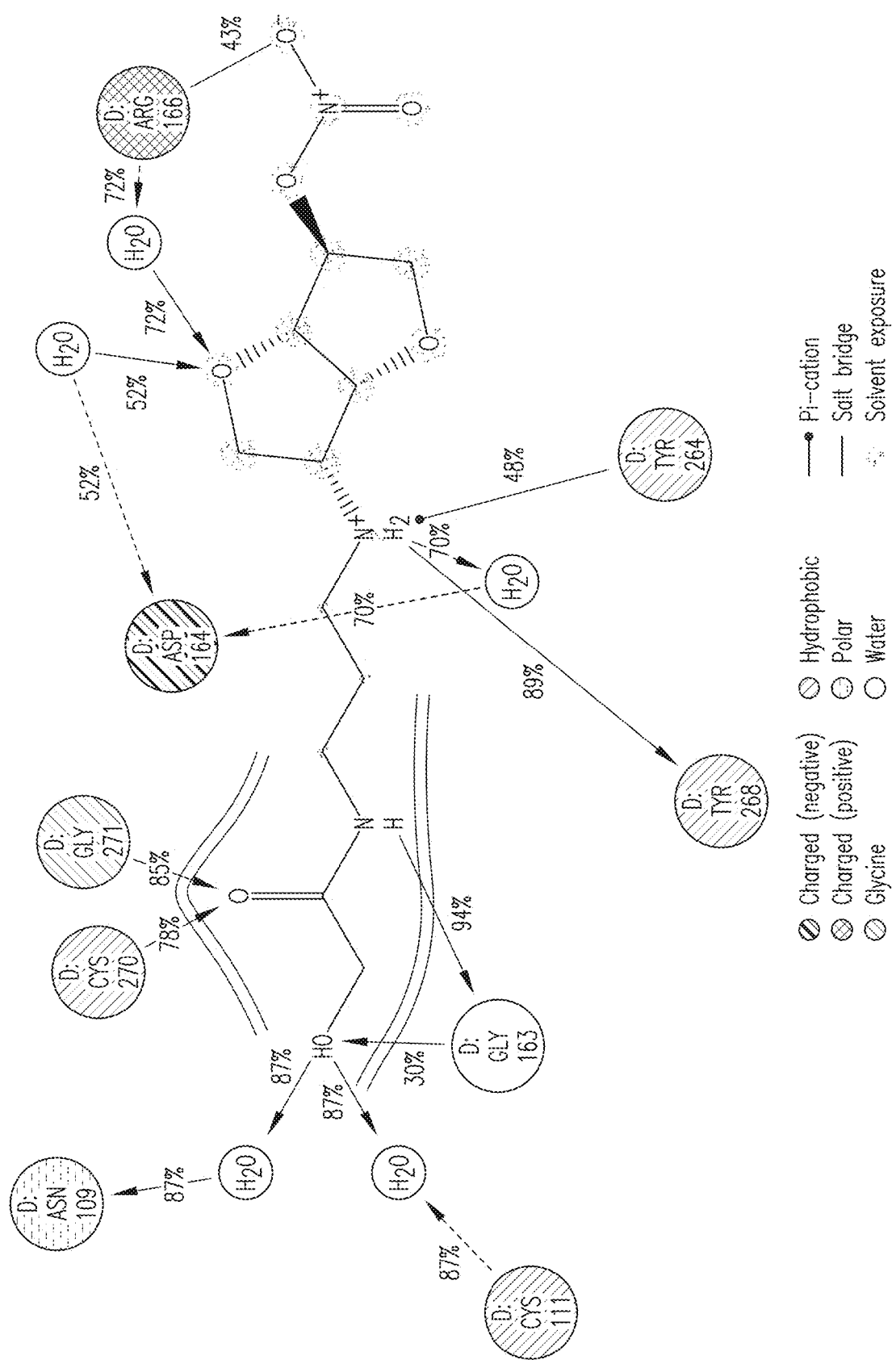
FIGS. 3A-B: A schematic of detailed ligand atom interactions of (FIG. 3A) CR-0305 and (FIG. 3B) GRL-0617 with the $PL^{pro}$ protein residues in the catalytic site is provided.
Figure 3B:
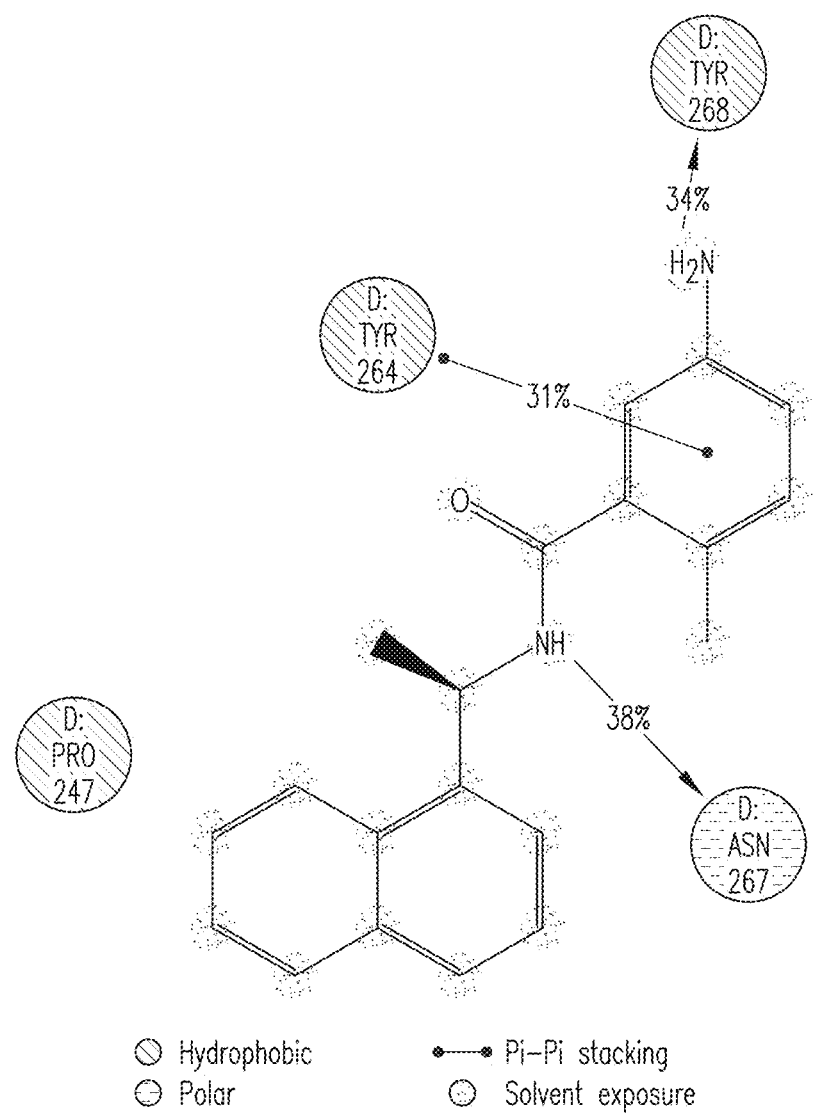

(FIG. 3A) and (FIG. 3B): These figures provide a schematic of detailed ligand atom interactions of (FIG. 3A) CR-0305 and (FIG. 3B) GRL-0617 with the PL$^{pro}$ protein residues in the catalytic site. Interactions that occur more than 30% of the simulation time in the selected trajectory (0 through 20 nanoseconds), are shown. The water network is defined between —OH and the active site (Cys-111) with over 87% contact strength (not seen for CR-0605, CR-0202 or GRL-0617) and this defines CR-0305 as the compound that provides the highest energy and most stable PL$^{pro}$ binding of the compounds studied.

Figure 4A:
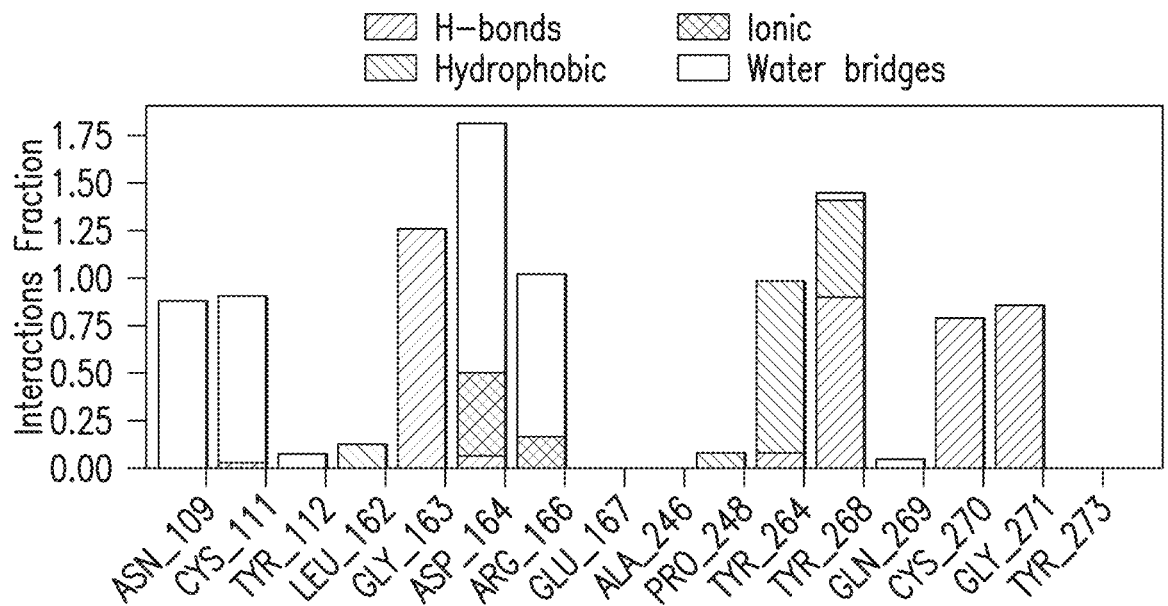
FIGS. 4A-D. The protein-ligand interactions with $PL^{pro}$ active site residues and CR-0305 and GRL-0617 are provided. Interactions at the catalytic site of $PL^{pro}$ with Cysteine-111 and the water bridge between CR-0305 (FIG. 4A) and $PL^{pro}$ proved to be the distinguishing feature when comparing with (FIG. 4B) GRL-0617.
Figure 4B:
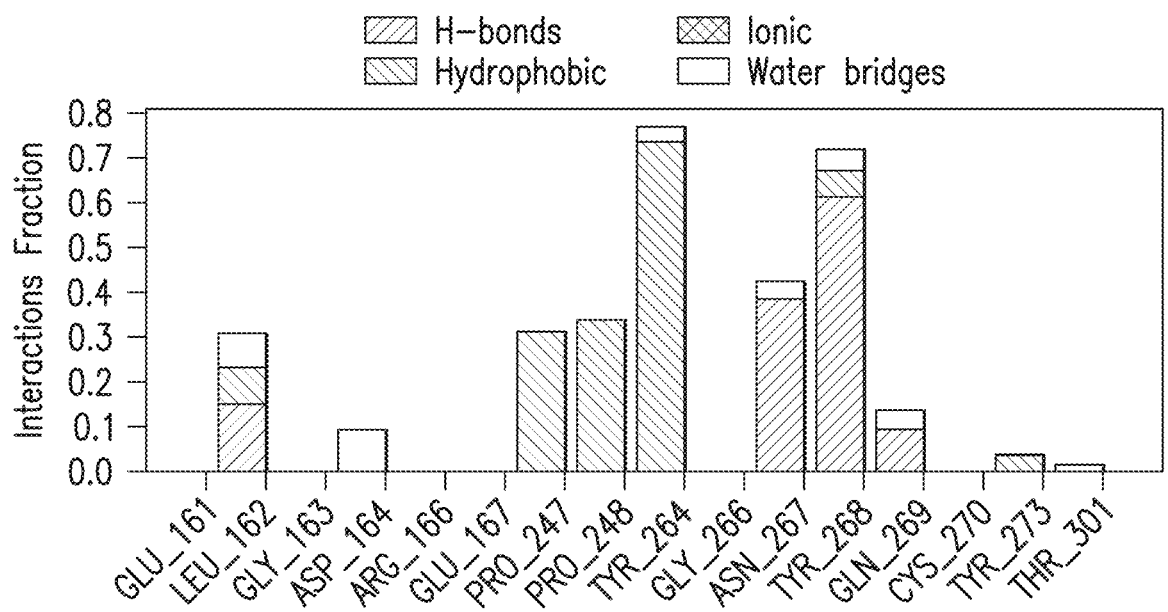
Figure 4C:
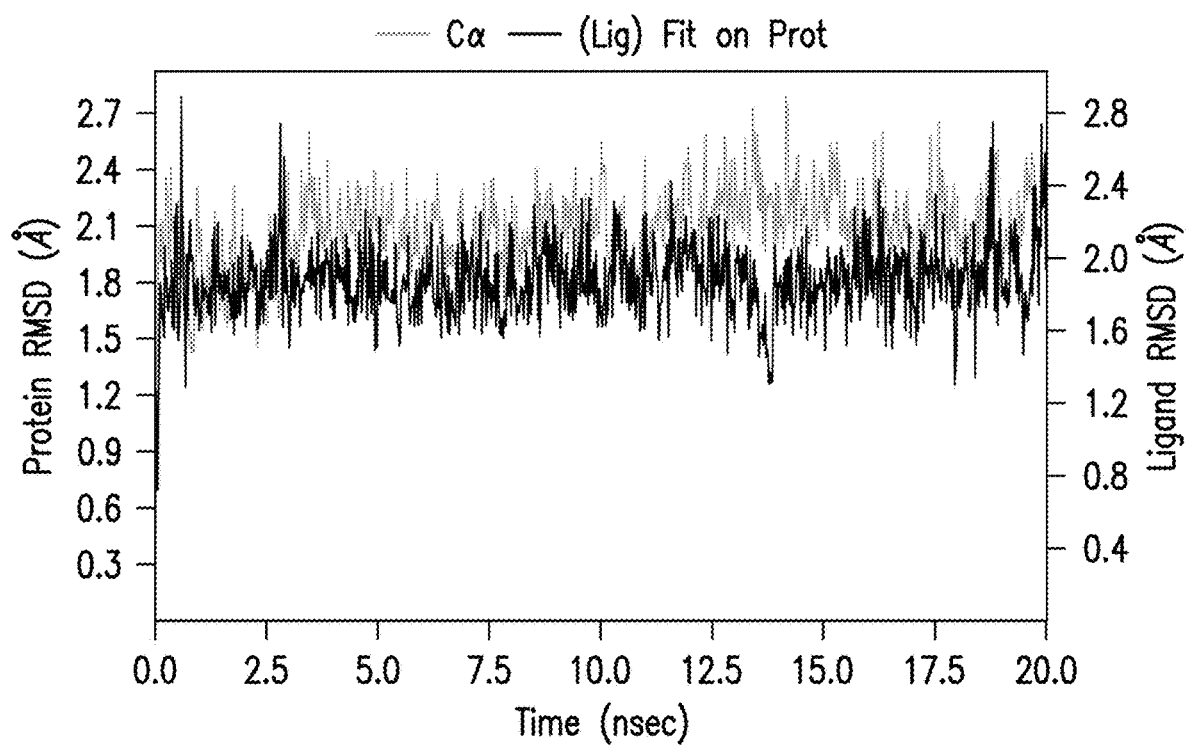
Figure 4D:
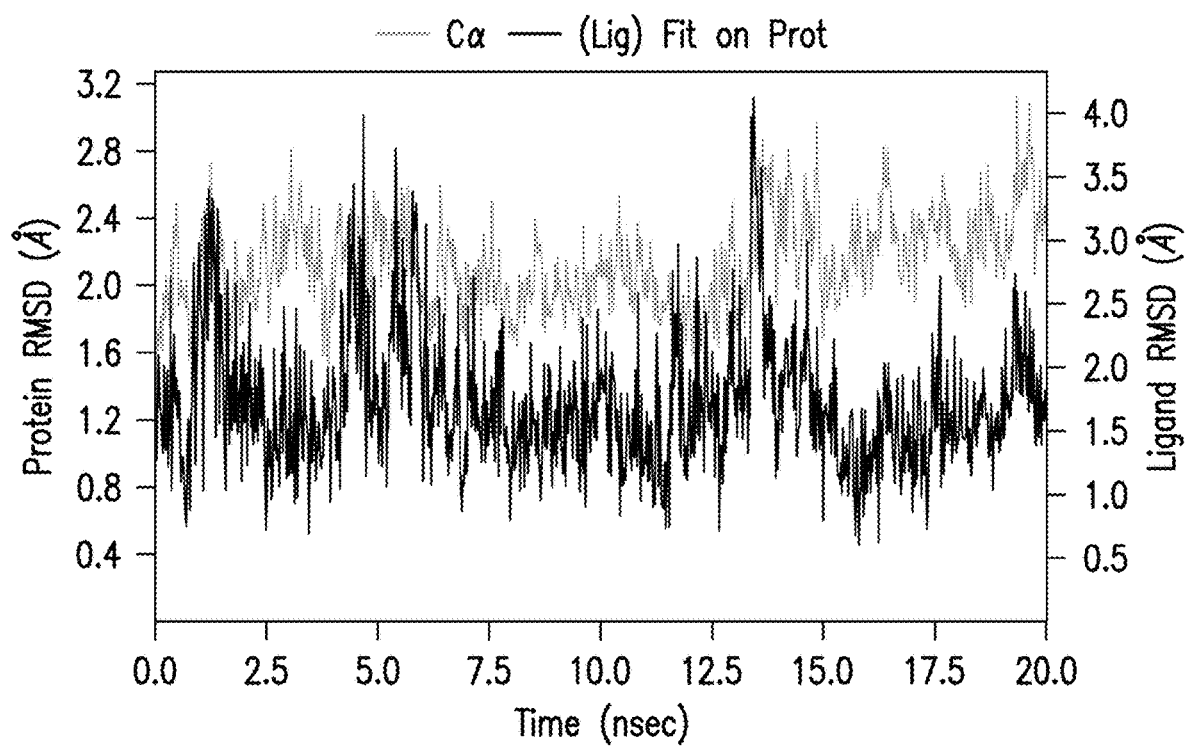

(FIG. 4A and FIG. 4B): The protein-ligand interactions with PL$^{pro}$ active site residues (or 'contacts') are categorized into four types: Hydrogen Bonds, Hydrophobic, Ionic and Water Bridges. Interactions at the catalytic site of PL$^{pro}$ hinge critically on Cysteine-111 and the water bridge between CR-0305 (FIG. 4A) and PL$^{pro}$ proved to be the distinguishing feature when comparing with (FIG. 4B) GRL-0617. (FIG. 4C) and (FIG. 4D): The Root Mean Square Deviation (RMSD) is used to measure the average change in displacement of a selection of atoms for a particular frame with respect to a reference frame. Changes larger than 1-3 Å indicate that the protein is undergoing a large conformational change during the simulation. Binding of CR-0305 (FIG. 4C) to the catalytic site of PL$^{pro}$ is more stable than binding of GRL-0617 (FIG. 4D) over time.

Numerous modifications and variations of the present invention are possible in light of the above teachings. It is therefore to be understood that within the scope of the appended claims, the invention may be practiced otherwise than as specifically described herein.

REFERENCE LIST

Baez-Santos, Y. M., S. E. St John and A. D. Mesecar (2015). "The SARS-coronavirus papain-like protease: structure, function and inhibition by designed antiviral compounds." *Antiviral Res* 115: 21-38.

Beigel, J. H., K. M. Tomashek, L. E. Dodd, A. K. Mehta, B. S. Zingman, A. C. Kalil, E. Hohmann, H. Y. Chu, A. Luetkemeyer, S. Kline, D. Lopez de Castilla, R. W. Finberg, K. Dierberg, V. Tapson, L. Hsieh, T. F. Patterson, R. Paredes, D. A. Sweeney, W. R. Short, G. Touloumi, D. C. Lye, N. Ohmagari, M. Oh, G. M. Ruiz-Palacios, T. Benfield, G. Fätkenheuer, M. G. Kortepeter, R. L. Atmar, C. B. Creech, J. Lundgren, A. G. Babiker, S. Pett, J. D. Neaton, T. H. Burgess, T. Bonnett, M. Green, M. Makowski, A. Osinusi, S. Nayak and H. C. Lane (2020). "Remdesivir for the Treatment of Covid—Final Report." *New England Journal of Medicine* 383(19): 1813-1826.

Chou, T. C. and P. Talalay (1984). "Quantitative analysis of dose-effect relationships: the combined effects of multiple drugs or enzyme inhibitors." *Adv. Enzyme Regul* 22:27-55.: 27-55.

Choudhary, M. I., M. Shaikh, A. tul-Wahab and A. ur-Rahman (2020). "In silico identification of potential inhibitors of key SARS-CoV-2 3CL hydrolase (Mpro) via molecular docking, MMGBSA predictive binding energy calculations, and molecular dynamics simulation." *PLoS ONE* 15(7): e0235030.

Feng, W. X., Y. Yang, J. Wen, Y. X. Liu, L. Liu and C. Feng (2020). "Implication of inhaled nitric oxide for the treatment of critically ill COVID-19 patients with pulmonary hypertension." *ESC Heart Failure* 8(n/a): 714-718.

Friesner, R. A., R. B. Murphy, M. P. Repasky, L. L. Frye, J. R. Greenwood, T. A. Halgren, P. C. Sanschagrin and D. T. Mainz (2006). "Extra Precision Glide: Docking and Scoring Incorporating a Model of Hydrophobic Enclosure for Protein-Ligand Complexes." *Journal of Medicinal Chemistry* 49(21): 6177-6196.

Gaisford, S. (2021). Chapter 17—Salt selection. *Remington The Science and Practice of Pharmacy*. A. Adejare, Academic Press: 307-314.

Giustino, G., S. P. Pinney, A. Lala, V. Y. Reddy, H. A. Johnston-Cox, J. Mechanick, I, J. L. Halperin and V. Fuster (2020). "Coronavirus and Cardiovascular Disease, Myocardial Injury, and Arrhythmia." *Journal Of The American College Of Cardiology* 76(17): 2011-2023.

Greene, T. W. and P. G. M. Wuts (1991). *Protective groups in organic synthesis*. New York, Wiley.

Greenwood, J. R., D. Calkins, A. P. Sullivan and J. C. Shelley (2010). "Towards the comprehensive, rapid, and accurate prediction of the favorable tautomeric states of drug-like molecules in aqueous solution." *Journal of Computer-Aided Molecular Design* 24(6): 591-604.

Hollingsworth, S. A. and R. O. Dror (2018). "Molecular Dynamics Simulation for All." *Neuron* 99(6): 1129-1143.

Keyaerts, E., L. Vijgen, L. Chen, P. Maes, G. Hedenstierna and M. Van Ranst (2004). "Inhibition of SARS-coronavirus infection in vitro by S-nitroso-N-acetylpenicillamine, a nitric oxide donor compound." *International Journal of Infectious Diseases* 8(4): 223-226.

MacMicking, J., Q. Xie and C. Nathan (1997). "Nitric Oxide and Macrophage Function." *Annual Review of Immunology* 15(1): 323-350.

Mantlo, E., N. Bukreyeva, J. Maruyama, S. Paessler and C. Huang (2020). "Antiviral activities of type I interferons to SARS-CoV-2 infection." *Antiviral Research* 179: 104811.

McClain, C. B. and N. Vabret (2020). "SARS-CoV-2: the many pros of targeting PLpro." *Nature Signal Transduct Target Ther* 5: 223-224.

Muro, A. and J.-L. Pérez-Arellano (2010). "Nitric oxide and respiratory helminthic diseases." *Journal of Biomedicine & Biotechnology* 2010: 958108-958108.

Rajput, B. S., S. R. Gaikwad, S. K. Menon and S. H. Chikkali (2014). "Sustainable polyacetals from isohexides." *Green Chemistry* 16(8): 3810-3818.

Saura, M., C. Zaragoza, A. McMillan, R. A. Quick, C. Hohenadl, J. M. Lowenstein and C. J. Lowenstein (1999). "An Antiviral Mechanism of Nitric Oxide: Inhibition of a Viral Protease." *Immunity* 10(1): 21-28.

Schmedtje, J. F., Jr., Y.-S. Ji, W.-L. Liu, R. N. DuBois and M. S. Runge (1997). "Hypoxia induces cyclooxygenase-2 via the NF-kappaB p65 transcription factor in human vascular endothelial cells." *J. Biol. Chem* 272(1): 601-608.

Shayakul, C., B. Clemencon and M. A. Hediger (2013). "The urea transporter family (SLC14): physiological, pathological and structural aspects." *Mol. Aspects Med* 34(2-3): 313-322.

Shelley, J. C., A. Cholleti, L. L. Frye, J. R. Greenwood, M. R. Timlin and M. Uchimaya (2007). "Epik: a software program for pKaprediction and protonation state generation for drug-like molecules." *Journal of Computer-Aided Molecular Design* 21(12): 681-691.

Shin, D., R. Mukherjee, D. Grewe, D. Bojkova, K. Baek, A. Bhattacharya, L. Schulz, M. Widera, A. R. Mehdipour, G. Tascher, P. P. Geurink, A. Wilhelm, G. van der Heden van Noort, H. Ovaa, S. Muller, K. P. Knobeloch, K. Rajalingam, B. A. Schulman, J. Cinatl, G. Hummer, S. Ciesek and I. Dikic (2020). "Papain-like protease regulates SARS-CoV-2 viral spread and innate immunity." *Nature* 587(7835): 657-662.

Stasko, N., K. McHale, S. J. Hollenbach, M. Martin and R. Doxey (2018). "Nitric Oxide-Releasing Macromolecule Exhibits Broad-Spectrum Antifungal Activity and Utility as a Topical Treatment for Superficial Fungal Infections." *Antimicrobial Agents and Chemotherapy* 62(7): e01026-01017.

Sun, Y., C. W. Lau, Y. Jia, Y. Li, W. Wang, J. Ran, F. Li, Y. Huang, H. Zhou and B. Yang (2016). "Functional inhibition of urea transporter UT-B enhances endothelial-dependent vasodilatation and lowers blood pressure via L-arginine-endothelial nitric oxide synthase-nitric oxide pathway." *Scientific Reports* 6: 18697.

Wiersinga, W. J., A. Rhodes, A. C. Cheng, S. J. Peacock and H. C. Prescott (2020). "Pathophysiology, Transmission, Diagnosis, and Treatment of Coronavirus Disease 2019 (COVID-19): A Review." *JAMA* 324(8): 782-793.

Wu, C., Y. Liu, Y. Yang, P. Zhang, W. Zhong, Y. Wang, Q. Wang, Y. Xu, M. Li, X. Li, M. Zheng, L. Chen and H. Li (2020). "Analysis of therapeutic targets for SARS-CoV-2 and discovery of potential drugs by computational methods." *Acta Pharmaceutica Sinica B* 10(5): 766-788.

Yang, L., E. S. Feura, M. J. R. Ahonen and M. H. Schoenfisch (2018). "Nitric Oxide-Releasing Macromolecular Scaffolds for Antibacterial Applications." *Advanced Healthcare Materials* 7(13): e1800155.

Yang, X., Y. Yu, J. Xu, H. Shu, J. Xia, H. Liu, Y. Wu, L. Zhang, Z. Yu, M. Fang, T. Yu, Y. Wang, S. Pan, X. Zou, S. Yuan and Y. Shang (2020). "Clinical course and outcomes of critically ill patients with SARS-CoV-2 pneumonia in Wuhan, China: a single-centered, retrospective, observational study." *Lancet Respir Med* 8(5): 475-481.

Yim, B., J.-H. Park, H. Jeong, J. Hong, M. Kim, M. Chang, R. S. Chuck and C. Y. Park (2018). "Effect of Nitric Oxide on *Acanthamoeba castellanii*." *Investigative Ophthalmology & Visual Science* 59(8): 3239-3248.

Zell, R., R. Markgraf, M. Schmidtke, M. Gorlach, A. Stelzner, A. Henke, H. H. Sigusch and B. Glück (2004). "Nitric oxide donors inhibit the coxsackievirus B3 proteinases 2A and 3C in vitro, virus production in cells, and signs of myocarditis in virus-infected mice." *Medical Microbiology and Immunology* 193(2): 91-100.

Zhao, D., N. D. Sonawane, M. H. Levin and B. Yang (2007). "Comparative transport efficiencies of urea analogues through urea transporter UT-B." *Biochimica et Biophysica Acta (BBA)—Biomembranes* 1768(7): 1815-1821.

What is claimed is:

1. A method of treating an infectious disease caused by a virus that contains a papain-like protease, wherein said treating is inhibiting, relieving, or ameliorating the disease, comprising: administering to a mammal in need thereof a therapeutically effective amount of a compound of formula I, II, III, IV, V or VI, wherein:

the compound is selected from formula I, II, III, IV, V, and VI:

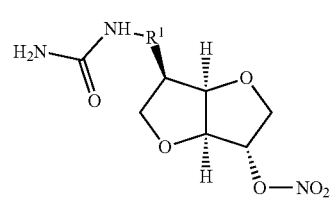

I

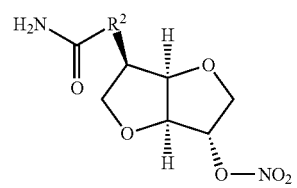

II

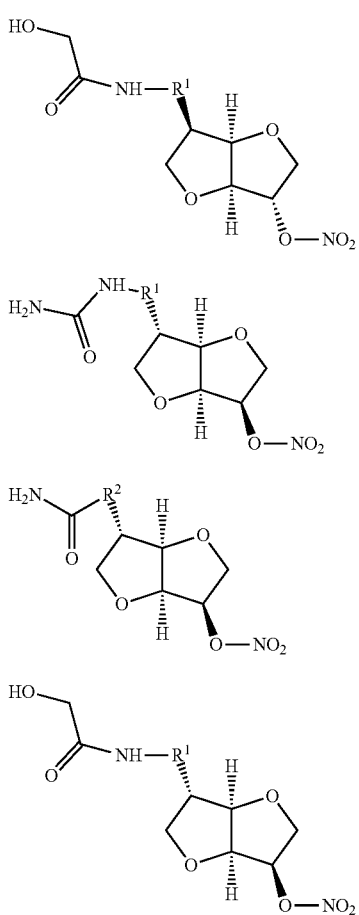

wherein:
R¹ is absent;
alternatively, R¹ is selected from: (CH₂)₂O, (CH₂)₂NH, (CH₂)₃O, (CH₂)₃NH, CH₂C(=O)O, and CH₂C(=O)NH; and, R² is selected from: (CH₂)₂O, (CH₂)₂NH, (CH₂)₃O, (CH₂)₃NH, CH₂C(=O)O, CH₂C(=O)NH, CH₂OC(=O)O, CH₂OC(=O)NH, CH₂NHC(=O)O, and CH₂NHC(=O)NH;

or a pharmaceutically acceptable salt thereof.

2. The method of claim 1, wherein the infectious disease causes cellular hypoxia in the patient.

3. The method of claim 1, wherein the infectious disease is COVID-19.

4. The method of claim 1, wherein the compound is of Formula I or IV or a pharmaceutically acceptable salt thereof.

5. The method of claim 4, wherein R¹ is absent.

6. The method of claim 4, wherein R¹ is selected from: (CH₂)₂O, (CH₂)₂NH, (CH₂)₃O, and (CH₂)₃NH.

7. The method of claim 4, wherein R¹ is (CH₂)₂O.

8. The method of claim 4, wherein R¹ is (CH₂)₂NH.

9. The method of claim 4, wherein R¹ is CH₂C(=O)O.

10. The method of claim 4, wherein R¹ is CH₂C(=O)NH.

11. The method of claim 1, wherein the compound is of Formula II or V or a pharmaceutically acceptable salt thereof.

12. The method of claim 11, wherein R² is selected from: (CH₂)₂O, (CH₂)₂NH, (CH₂)₃O, (CH₂)₃NH, CH₂OC(=O)O, CH₂OC(=O)NH, CH₂NHC(=O)O, and CH₂NHC(=O)NH.

13. The method of claim 11, wherein R² is CH₂C(=O)O.

14. The method of claim 11, wherein R² is CH₂C(=O)NH.

15. The method of claim 1, wherein the compound is of Formula III or VI or a pharmaceutically acceptable salt thereof.

16. The method of claim 15, wherein R¹ is absent.

17. The method of claim 15, wherein R¹ is selected from: (CH₂)₂O, (CH₂)₂NH, (CH₂)₃O, and (CH₂)₃NH.

18. The method of claim 15, wherein R¹ is CH₂C(=O)O.

19. The method of claim 15, wherein R¹ is CH₂C(=O)NH.

* * * * *